(12) United States Patent
Duran et al.

(10) Patent No.: US 10,751,338 B2
(45) Date of Patent: Aug. 25, 2020

(54) SUSTAINED-RELEASE VORICONAZOLE-CONTAINING THERMOGEL AND USES THEREOF

(71) Applicants: Sue H. Duran, Auburn, AL (US); Allison Stewart, Queensland (AU); William R. Ravis, Auburn, AL (US); Eva Abarca, Barcelona (ES); Rosemary Cuming, Scone (AU); Mariano Mora Pereira, Auburn, AL (US)

(72) Inventors: Sue H. Duran, Auburn, AL (US); Allison Stewart, Queensland (AU); William R. Ravis, Auburn, AL (US); Eva Abarca, Barcelona (ES); Rosemary Cuming, Scone (AU); Mariano Mora Pereira, Auburn, AL (US)

(*) Notice: Subject to any disclaimer, the term of this patent is extended or adjusted under 35 U.S.C. 154(b) by 0 days.

(21) Appl. No.: 16/117,443

(22) Filed: Aug. 30, 2018

(65) Prior Publication Data
US 2019/0060312 A1 Feb. 28, 2019

Related U.S. Application Data

(60) Provisional application No. 62/552,086, filed on Aug. 30, 2017.

(51) Int. Cl.
| | | |
|---|---|---|
| *A61K 31/506* | (2006.01) | |
| *A61P 27/02* | (2006.01) | |
| *A61P 31/10* | (2006.01) | |
| *A61K 9/06* | (2006.01) | |
| *A61K 47/34* | (2017.01) | |
| *A61K 9/00* | (2006.01) | |

(52) U.S. Cl.
CPC .......... *A61K 31/506* (2013.01); *A61K 9/0019* (2013.01); *A61K 9/0048* (2013.01); *A61K 9/06* (2013.01); *A61K 47/34* (2013.01); *A61P 27/02* (2018.01); *A61P 31/10* (2018.01)

(58) Field of Classification Search
CPC ......... A61K 31/506; A61K 9/06; A61P 27/02; A61P 31/10
See application file for complete search history.

(56) References Cited

FOREIGN PATENT DOCUMENTS

CN 1813751 A * 8/2006

OTHER PUBLICATIONS

Cuming et al (Invest Ophthalmol Vis Sci. 2017;58:2746-2754, published May 2017) (Year: 2017).*
Cuming et al (J Vet Intern Med 2015;29:1122-1256), referred to as Cuming 2015) (Year: 2015).*
Equi-Analytical Laboratories (https://equi-analytical.com/weight-and-height-ranges-for-common-breeds/, obtained from the internet Nov. 19, 2019) (Year: 2019).*
Cayman Chemical (Voriconazle Product Information, Jul. 3, 2014) (Year: 2014).*
Brooks DE. Equine keratomycosis: An international problem. *Equine Vet Educ* 2009;21:243-246.
Keay LJ, Gower EW, Iovieno A, et al. Clinical and microbiological characteristics of fungal keratitis in the United States, 2001-2007: a multicenter study. *Ophthalmology* 2011;118:920-926.
Thomas PA, Kaliamurthy J. Mycotic keratitis: epidemiology, diagnosis and management. *Clin Microbiol Infect* 2013;19:210-220.
Clode AB, Davis JL, Salmon J, Michau TM, Gilger BC. Evaluation of concentration of voriconazole in aqueous humor after topical and oral administration in horses. *Am J Vet Res* 2006;67:296-301.
Zeiss C, Neaderland M, Yang FC, Terwilliger G, Compton S. Fungal polymerase chain reaction testing in equine ulcerative keratitis. *Vet Ophthalmol* 2013;16:341-351.
Rosa M, Cardozo LM, Pereira JD, et al. Fungal flora of normal eyes of healthy horses from the State of Rio de Janeiro, Brazil. *Vet Ophthalmol* 2003;6:51-55.
Voelter Ratson K, Pot SA, Florin M, Spiess BM. Equine keratomycosis in Switzerland: a retrospective evaluation of 35 horses (Jan. 2000-Aug. 2011). *Equine Vet J* 2013;45:608-612.
Wada S, Hobo S, Ode H, Niwa H, Moriyama H. Equine keratomycosis in Japan. *Vet Ophthalmol* 2013;16:1-9.
Andrew SE, Brooks DE, Smith PJ, Gelatt KN, Chmielewski NT, Whittaker CJG. Equine ulcerative keratomycosis: visual outcome and ocular survival in 39 cases (1987-1996). *Equine Vet J* 1998;30:109-116.
Brooks DE, Plummer CE, Mangan BG, Ben-Shlomo G. Equine subepithelial keratomycosis. *Vet Ophthalmol* 2013;16:93-96.
Galán A, Martin-Suárez EM, Gallardo JM, Molleda JM. Clinical findings and progression of 10 cases of equine ulcerative keratomycosis (2004-2007). *Equine Vet Educ* 2009;21:236-242.
Sherman AB, Clode AB, Gilger BC. Impact of fungal species cultured on outcome in horses with fungal keratitis. *Vet Ophthalmol* 2016.
Beech J, Sweeney C. Keratomycoses in 11 horses. *Equine Vet J* 1983;15:39-44.
Reed Z, Thomasy SM, Good KL, et al. Equine keratomycoses in California from 1987 to 2010 (47 cases). *Equine Vet J* 2013;45:361-366.
Andrew SE, Ramsey DT, Hauptman JG, Brooks DE. Density of corneal endothelial cells and corneal thickness in eyes of euthanatized horses. *Am J Vet Res* 2001;62:479-482.
Patipa LA, Sherlock CE, Witte SH, Pirie GD, Berghaus RD, Peroni JF. Risk factors for colic in equids hospitalized for ocular disease. *J Am Vet Med Assoc* 2012;240:1488-1493.
Ledbetter EC, Irby NL, Kim SG. In vivo confocal microscopy of equine fungal keratitis. *Vet Ophthalmol* 2011;14:1-9.

(Continued)

Primary Examiner — Marcos L Sznaidman
Assistant Examiner — Rayna Rodriguez
(74) *Attorney, Agent, or Firm* — Barnes & Thornburg LLP

(57) ABSTRACT

The present disclosure provides veterinary formulations comprising a therapeutically effective amount of a voriconazole and a polymer. The disclosure also provides methods, and kits for the treatment of disease, such as for treating a fungal infection in an animal utilizing the veterinary formulations.

9 Claims, 24 Drawing Sheets

(56) References Cited

OTHER PUBLICATIONS

Al-Badriyeh D, Neoh CF, Stewart K, Kong DC. Clinical utility of voriconazole eye drops in ophthalmic fungal keratitis. *Clin Ophthalmol* 2010;4:391-405.

Mandy RA, Nada WM, Wageh MM. Topical amphotericin B and subconjunctival injection of fluconazole (combination therapy) versus topical amphotericin B (monotherapy) in treatment of keratomycosis. *J Ocul Pharmacol Ther* 2010;26:281-285.

Thomas PA. Current Perspectives on Ophthalmic Mycoses. *Clin Microbiol Rev* 2003;16:730-797.

Sun CQ, Lalitha P, Prajna NV, et al. Association between in vitro susceptibility to natamycin and voriconazole and clinical outcomes in fungal keratitis. *Ophthalmology* 2014;121:1495-1500 e1491.

Gilmour MA. Subconjunctival voriconazole for the treatment of mycotic keratitis in a horse. *Equine Vet Educ* 2012;24:489-492.

Smith KM, Pucket JD, Gilmour MA. Treatment of six cases of equine corneal stromal abscessation with intracorneal injection of 5% voriconazole solution. *Vet Ophthalmol* 2014;17 Suppl 1:179-185.

Tsujita H, Plummer CE. Corneal stromal abscessation in two horses treated with intracorneal and subconjunctival injection of 1% voriconazole solution. *Vet Ophthalmol* 2013;16:451-458.

Lai J, Pandya V, McDonald R, Sutton G. Management of Fusarium keratitis and its associated fungal iris nodule with intracameral voriconazole and amphotericin B. *Clin Exp Optom* 2014;97:181-183.

Latimer FG, Colitz CMH, Campbell NB, Papich MG. Pharmacokinetics of fluconazole following intravenous and oral administration and body fluid concentrations of fluconazole following repeated oral dosing in horses. *Am J Vet Res* 2001;62:1606-1611.

Pearce JW, Giuliano EA, Moore CP. In vitro susceptibility patterns of *Aspergillus* and *Fusarium* species isolated from equine ulcerative keratomycosis cases in the midwestern and southern United States with inclusion of the new antifungal agent voriconazole. *Vet Ophthalmol* 2009;12:318-324.

Senthilkumari S, Lalitha P, Prajna NV, et al. Single and multidose ocular kinetics and stability analysis of extemporaneous formulation of topical voriconazole in humans. *Curr Eye Res* 2010;35:953-960.

Kompella UB, Kadam RS, Lee VH. Recent advances in ophthalmic drug delivery. *Ther Deliv* 2010;1:435-456.

Gaudana R, Ananthula HK, Parenky A, Mitra AK. Ocular drug delivery. *AAPS J* 2010;12:348-360.

Pawar P, Kashyap H, Malhotra S, Sindhu R. Hp-beta-CD-voriconazole in situ gelling system for ocular drug delivery: in vitro, stability, and antifungal activities assessment. *Biomed Res Int* 2013;2013:341218.

Rieke ER, Amaral J, Becerra SP, Lutz RJ. Sustained subconjunctival protein delivery using a thermosetting gel delivery system. *J Ocul Pharmacol Ther* 2010;26:55-64.

Gaudana R, Jwala J, Boddu SH, Mtra AK. Recent perspectives in ocular drug delivery. *Pharm Res* 2009;26:1197-1216.

Al-Badriyeh D, Leung L, Roydhouse T, et al. Prospective open-label study of the administration of two-percent voriconazole eye drops. *Antimicrob Agents Chemother* 2009;53:3153-3155.

Vorwerk CK, Streit F, Binder L, Tuchen S, Knop C, Behrens-Baumann W. Aqueous humor concentration of voriconazole after topical administration in rabbits. *Graefes Arch Clin Exp Ophthalmol* 2008;246:1179-1183.

Andrade LM, Rocha KA, De Sa FA, et al. Voriconazole-Loaded Nanostructured Lipid Carriers for Ocular Drug Delivery. *Cornea* 2016;35:866-871.

Kumar R, Sinha VR. Preparation and optimization of voriconazole microemulsion for ocular delivery. *Colloids Surf B Biointerfaces* 2014;117:82-88.

Kumar R, Sinha VR. Solid lipid nanoparticle: an efficient carrier for improved ocular permeation of voriconazole. *Drug Dev Ind Pharm* 2016.

Booth TM, Butson RJ, Clegg PD, Schramme MC, Smith RK. Treatment of sepsis in the small tarsal joints of 11 horses with gentamicin-impregnated polymethylmethacrylate beads. *Vet Rec* 2001;148:376-380.

Summerhays GE. Treatment of traumatically induced synovial sepsis in horses with gentamicin impregnated collagen sponges. *Vet Rec* 2000;147:184-188.

Hemingway RG. The influences of dietary intakes and supplementation with selenium and vitamin E on reproduction diseases and resproductive efficiency in cattle and sheep. *Vet Res Commun* 2003;27:159-174.

Meyers PJ, Bowman T, Blodgett G, et al. Use of the GnRH analogue, deslorelin acetate, in a slow-release implant to accelerate ovulation in oestrous mares. *Vet Rec* 1997;140:249-252.

Lucas X. Clinical use of deslorelin (GnRH agonist) in companion animals: a review. *Reprod Domest Anim* 2014;49 Suppl 4:64-71.

Gilger BC, Salmon JH, Wilkie DA, et al. A novel bioerodible deep scleral lamellar cyclosporine implant for uveitis. *Invest Ophthalmol Vis Sci* 2006;47:2596-2605.

Gilger BC, Stoppini R, Wilkie DA, et al. Treatment of immune-mediated keratitis in horses with episcleral silicone matrix cyclosporine delivery devices. *Vet Ophthalmol* 2014;17 Suppl 1:23-30.

Mackenzie CJ, Carslake HB, Robin M, Kent RJ, Malalana F. Episcleral cyclosporine A implants for the management of unilateral keratoconjunctivitis sicca in an 8-year-old mare. *Vet Ophthalmol* 2016.

Bhattarai N, Gunn J, Zhang M. Chitosan-based hydrogels for controlled, localized drug delivery. *Adv Drug Deliv Rev* 2010;62:83-99.

Duvvuri S, Janoria KG, Pal D, Mitra AK. Controlled delivery of ganciclovir to the retina with drug-loaded Poly(d,L-lactide-co-glycolide) (PLGA) microspheres dispersed in PLGA-PEG-PLGA Gel: a novel intravitreal delivery system for the treatment of cytomegalovirus retinitis. *J Ocul Pharmacol Ther* 2007;23:264-274.

Gao Y, Sun Y, Ren F, Gao S. PLGA-PEG-PLGA hydrogel for ocular drug delivery of dexamethasone acetate. *Drug Dev Ind Pharm* 2010;36:1131-1138.

Ward MA, Georgiou TK. Thermoresponsive Polymers for Biomedical Applications. *Polymers* 2011;3:1215-1242.

Pratoomsoot C, Tanioka H, Hori K, et al. A thermoreversible hydrogel as a biosynthetic bandage for corneal wound repair. *Biomaterials* 2008;29:272-281.

Cho H, Kwon GS. Thermosensitive poly-(d,l-lactide-co-glycolide)-block-poly(ethylene glycol)-block-poly-(d,l-lactide-co-glycolide) hydrogels for multi-drug delivery. *J Drug Target* 2014;22:669-677.

Park MH, Joo MK, Choi BG, Jeong B. Biodegradable Thermogels. *Acc Chem Res* 2012;45:424-433.

Han SB, Shin YJ, Hyon JY, Wee WR. Cytotoxicity of voriconazole on cultured human corneal endothelial cells. *Antimicrob Agents Chemother* 2011;55:4519-4523.

Han SB, Yang HK, Hyon JY, Shin YJ, Wee WR. Toxicity of voriconazole on corneal endothelial cells in an animal model. *Br J Ophthalmol* 2012;96:905-908.

Passler NH, Chan HM, Stewart AJ, et al. Distribution of voriconazole in seven body fluids of adult horses after repeated oral dosing. *J Vet Pharmacol Ther* 2010;33:35-41.

Tyler B, Fowers KD, Li KW, et al. A thermal gel depot for local delivery of paclitaxel to treat experimental brain tumors in rats. *J Neurosurg* 2010;113:210-217.

Tyler BM, Hdeib A, Caplan J, et al. Delayed onset of paresis in rats with experimental intramedullary spinal cord gliosarcoma following intratumoral administration of the paclitaxel delivery system OncoGel. J Neurosurg Spine 2012;16:93-101.

Whiting K, Molnar J, McCall C. Alabama equine industry: inventory, impact and prospects. *Auburn University Bulletin*: Alabama Agricultural Experiment Station; 2006.

McCall C, Molnar J, Pendergrass R, Broadway R. Economic impacts of the Alabama horse industry. *ANR*: Alabama Cooperative Extension System; 1999.

Duench S, Simpson T, Jones LW, Flanagan JG, Fonn D. Assessment of variation in bulbar conjunctival redness, temperature and blood flow. *Optom Vis Sci* 2007;84:511-516.

(56) References Cited

OTHER PUBLICATIONS

Efron N, Brennan NA, Hore J, Rieper K. Temperature of the Hyperemic Bulbar Conjunctiva. *Curr Eye Res* 1988;7:615-618.

Schwartz B, Feller M. Temperature gradients in the rabbit eye. *Invest Ophthalmol* 1962;1:513-521.

Garner J, Skidmore S. White Paper: Thermogel Mixtures Impact on Rheology. AKINA Inc.; 2013.

Kim H, Csaky KG, Gilger BC, et al. Preclinical evaluation of a novel episcleral cyclosporine implant for ocular graft-versus-host disease. *Invest Ophthalmol Vis Sci* 2005;46:655-662.

Lee SS, Kim H, Wang NS, et al. A Pharmacokinetic and Safety Evaluation of an Episcleral Cyclosporine Implant for Potential Use in High Risk Keratoplasty Rejection. *Invest Ophthalmol Vis Sci* 2007;48:2023-2029.

Zhang W, Prausnitz MR, Edwards A. Model of transient drug diffusion across cornea. *J Control Release* 2004;99:241-258.

Thakur A, Kadam RS, Kompella UB. Influence of drug solubility and lipophilicity on transscleral retinal delivery of six corticosteroids. *Drug Metab Dispos* 2011;39:771-781.

Qiao M, Chen D, Ma X, Liu Y. Injectable biodegradable temperature responsive PLGA-PEG-PLGA copolymers: synthesis and effect of copolymer composition on the drug release from the copolymer based hydrogels. *Int J Pharm* 2005;294:103-112.

Duvvuri S, Janoria KG, Mitra AK. Development of a novel formulation containing poly(d,l-lactide-co-glycolide) microspheres dispersed in PLGA-PEG-PLGA gel for sustained delivery of ganciclovir. *J Control Release* 2005;108:282-293.

Muankaew C, Jansook P, Loftsson T. Evaluation of γ-cyclodextrin effect on permeation of lipophilic drugs: application of cellophane/fused octanol membrane. *Pharm Dev Technol* 2016;1-9.

Ghosn MG, Tuchin VV, Larin KV. Nondestructive quantification of analyte diffusion in cornea and sclera using optical coherence tomography. *Invest Ophthalmol Vis Sci* 2007;48:2726-2733.

Jiang J, Geroski DH, Edelhauser HF, Prausnitz MR. Measurement and prediction of lateral diffusion within human sclera. *Invest Ophthalmol Vis Sci* 2006;47:3011-3016.

Mutlu FM, Yildiran ST, Saracli MA, et al. The first case of fungal endophthalmitis caused by Emericella nidulans after cataract surgery. *J Mycol Med* 2016.

\* cited by examiner

A

B

SUSTAINED-RELEASE VORICONAZOLE-CONTAINING THERMOGEL AND USES THEREOF

CROSS-REFERENCE TO RELATED APPLICATIONS

This application claims the benefit under 35 USC § 119(e) of U.S. Provisional Application Ser. No. 65/552,086, filed on Aug. 30, 2017, the entire disclosure of which is incorporated herein by reference.

TECHNICAL FIELD

The invention relates to veterinary formulations comprising a therapeutically effective amount of a voriconazole and a polymer. The invention includes formulations, methods, and kits for the treatment of disease, such as for treating a fungal infection in an animal.

BACKGROUND AND SUMMARY OF THE INVENTION

Keratomycosis is a vision-threatening disease caused by fungal infection of the cornea. Fungal keratitis is an emerging cause of corneal disease in horses, with the reported incidence in North America rising from 13% of keratitis cases in the 40 years preceding 2006 to approximately 25% in 2013. Keratomycosis is particularly prevalent in tropical or subtropical environments, such as the southern United States. For example, in the state of Alabama, keratomycosis accounted for 40% of the equine corneal disease caseload presenting to the Auburn University Large Animal Teaching Hospital (AULATH) during the 2012-2013 academic year.

Equines, in particular horses, are believed to be prone to fungal ocular infections due to their large globe size, unique orbital shape and resultant globe exposure, suspected tear film instability and living environment. Fungi are ubiquitous in the equine environment (e.g. in hay, soil and bedding) and are also part of the normal ocular surface microbiota of the horse. More than 30 genera of fungi have been implicated in equine keratomycosis, with the most common being the filamentous fungi *Aspergillus, Fusarium* and *Penicillium* and the yeast *Candida*.

Development of keratomycosis requires disruption of the normal defense mechanisms of the equine cornea and conjunctiva such as the intact corneal epithelium, normal bacterial microbiota, flushing of commensal organisms through tear flow and eyelid movement, and tear film macrophages, lysozymes and immunoglobulins. Following disruption of one or more of these defense mechanisms, commensal or introduced (environmental) fungi are able to adhere to the cornea, proliferate and invade the conical stroma. Fungal organisms, damaged keratocytes and inflammatory cells attracted to the area by the fungi then release proteases which facilitate vertical movement of fungi through the conical stroma and Descemet's membrane. This may ultimately result in fungal migration into the anterior chamber, lens and iris, with subsequent development of severe endophthalmitis.

Clinical manifestations of equine keratomycosis include corneal ulceration (with or without keratomalacia), conical microerosions, superficial punctate keratitis, stromal abscessation, stromal plaque formation, and conical perforation with iris prolapse. Of these, stromal ulcerative keratomycosis is the most common manifestation, comprising 50.80% of reported cases of equine keratomycosis.

Furthermore, equine keratomycosis is a source of severe morbidity in horses Fungal organisms and infiltrating immune cells are capable of initiating both vigorous inflammatory responses and protease overproduction in the cornea. In turn, this may lead to the development of acute complications in affected eyes including rapid keratomalacia (melting of the cornea), unresolving ulceration, abscess formation, uncontrolled anterior uveitis, endophthalmitis and corneal perforation. Long term sequelae may include corneal scarring, cataract or synechiae formation, phthisis bulbi and vision loss. In various case studies reporting outcomes in horses affected with equine keratomycosis, success rates (as defined by restoration of functional vision and/or ocular survival) in these equine populations varied from 50% to greater than 90%, with the majority of case series reporting retention of functional vision in <70% of cases. In light of the severity of potential sequelae of keratomycosis described above, these success rates are undesirable.

Equine keratomycosis treatment is challenging, prolonged and expensive and requires compliance from both horses and their handlers. The average duration of treatment varies from 48 to 72 days, and up to 192 days of treatment has been described. The average time required in the hospital varies from 15 to 21 days, which represents an investment of thousands of dollars and a source of considerable stress for the horse and has been defined as a risk factor for development of colic.

Fungal keratitis can be treated with either medical therapy alone or a combination of medical and surgical therapy. Although surgical procedures are immediately indicated in animals with acute corneal perforation or in those with imminent or pre-existing rupture of a stromal abscess into the anterior chamber, medical treatment with antifungal agents is a major therapeutic option in most cases, whereby success depends on the agent's ability to penetrate the conical epithelium and achieve therapeutic concentrations in the anterior segment of the eye. In order to reach therapeutic concentrations in the cornea and anterior chamber, treatment typically involves application of topical medication every 1-2 hours in acute disease, decreasing ultimately to every 6-12 hours, with potential concurrent administration of oral antifungals, anti-inflammatory agents, and antibiotics.

Voriconazole is a second generation triazole antifungal drug and is a relatively new antifungal agent in equine and human ophthalmology. Despite the excellent corneal penetration of voriconazole, several additional barriers exist in the eye which must be overcome in order to obtain higher or more sustained therapeutic voriconazole concentrations in the cornea and anterior chamber following topical delivery. Upon topical administration, pre-corneal factors and anatomical barriers negatively affect the bioavailability of topical formulations. Anatomical drug transport barriers include corneal and conjunctival epithelial tight junctions and clearance from the vasculature in the conjunctiva. Furthermore, despite effective corneal penetration, sustained drug delivery is still severely limited by ocular barriers and this effect is short lived, with studies is rabbits demonstrating the need for administration of voriconazole every 30 minutes in order to achieve a sustained high level of voriconazole in the anterior chamber.

Therefore, there exists a need for new compositions and formulations that provide therapeutic options for treating keratomycosis. Accordingly, the present disclosure provides veterinary formulations comprising a therapeutically effective amount of voriconazole, as well as kits, and also methods of using the formulations and kits, which exhibit desirable properties and provide related advantages for improvement in administration and treatment of keratomycosis.

The present disclosure provides veterinary formulations comprising a therapeutically effective amount of voriconazole and a polymer. The disclosure also provides kits comprising voriconazole and a polymer, as well as methods of treating a fungal infection in an animal, said method comprising the step of administering a veterinary formulation comprising a therapeutically effective amount of voriconazole and a polymer to the animal utilizing the veterinary formulations and kits of the present disclosure.

The veterinary formulations, kits, and methods according to the present disclosure provide several advantages compared to other formulations and methods known in the art. First, a sustained-release veterinary formulation comprising voriconazole has great potential to improve comfort and ultimate outcome for animals suffering from keratomycosis, especially horses. Second, such a formulation can provide a treatment which would be available to all affected animals, regardless of budget, as it could be administered in the field. Third, the formulation, given via subconjunctival injection, would negate the need for frequent topical application of voriconazole to animals. This would result in minimizing stress in patients and improving compliance by decreasing the volume, frequency, and cost of medication required for treatment. Fourth, utilization of thermogel polymers (e.g., thermosensitive biodegradable hydrogels or 'thermogels') can advantageously be administered as a liquid, followed by conversion to a gel deposit upon reaching the appropriate temperature. As a result, the thermogel polymers can maintain a sustained release of drug at the site of administration in the animal, for example over weeks to months. The sustained release of voriconazole to an animal suffering from keratomycosis would increase the local bioavailability of the medication, decrease systemic side effects, and improve client compliance.

The following numbered embodiments are contemplated and are non-limiting:

1. A veterinary formulation comprising i) a therapeutically effective amount of voriconazole and ii) a polymer.

2. The veterinary formulation of clause 1, wherein the veterinary formulation further comprises an alcohol.

3. The veterinary formulation of clause 2, wherein the alcohol is ethanol.

4. The veterinary formulation of any one of clauses 1 to 3, wherein the veterinary formulation further comprises a second therapeutic agent.

5. The veterinary formulation of clause 4, wherein the second therapeutic agent is selected from the group consisting of an oral antifungal agent, an anti-inflammatory agent, and an antibiotic.

6. The veterinary formulation of any one of clauses 1 to 5, wherein the polymer is a thermogel polymer.

7. The veterinary formulation of clause 6, wherein the thermogel polymer is selected from the group consisting of poly(ethylene glycol) (PEG), poly(propylene glycol) (PPG), poly (N-isopropyl acrylamide) (PNIPAAm), poly(N,N-diethyl acrylamide) (PDEAM), poly(N-ethyl methacrylamide) (PNEMAM), poly(methyl vinyl ether) (PMVE), poly(2-ethoxyethyl vinyl ether) (PEOVE), poly(N-vinyl isobutyramide) (PNVIBAM), poly(N-vinyl n-butyramide) (PNVBAM), poly(N-vinyl caprolactam) (PNVCa), and poly (hydroxypropyl methacrylamide) (HPMA), poly(lactide-co-glycolide)-b-poly(ethylene glycol)-b-poly(lactide-co-glycolide) (PLGA-PEG-PLGA), poly(DL-lactide)-b-Poly(ethylene glycol)-b-Poly(DL-lactide) (P(DL)LA-PEG-P(DL)LA), and poly(lactide-co-caprolactone)-b-Poly(ethylene glycol)-b-Poly(lactide-co-caprolactone) (PLCL-PEG-PLCL).

8. The veterinary formulation of clause 6, wherein the thermogel polymer is a combination of two or more thermogel polymers selected from the group consisting of poly(ethylene glycol) (PEG), poly(propylene glycol) (PPG), poly (N-isopropyl acrylamide) (PNIPAAm), poly(N,N-diethyl acrylamide) (PDEAM), poly(N-ethyl methacrylamide) (PNEMAM), poly(methyl vinyl ether) (PMVE), poly(2-ethoxyethyl vinyl ether) (PEOVE), poly(N-vinyl isobutyramide) (PNVIBAM), poly(N-vinyl n-butyramide) (PNVBAM), poly(N-vinyl caprolactam) (PNVCa), and poly (hydroxypropyl methacrylamide) (HPMA), poly(lactide-co-glycolide)-b-poly(ethylene glycol)-b-poly(lactide-co-glycolide) (PLGA-PEG-PLGA), poly(DL-lactide)-b-Poly(ethylene glycol)-b-Poly(DL-lactide) (P(DL)LA-PEG-P(DL)LA), and poly(lactide-co-caprolactone)-b-Poly(ethylene glycol)-b-Poly(lactide-co-caprolactone) (PLCL-PEG-PLCL).

9. The veterinary formulation of clause 6, wherein the thermogel polymer is PLGA-PEG-PLGA.

10. The veterinary formulation of clause 9, wherein the PLGA-PEG-PLGA has a molecular weight of 1100:1000:1100 Da.

11. The veterinary formulation of clause 9, wherein the PLGA-PEG-PLGA has a molecular weight of 1500:1500:1500 Da.

12. The veterinary formulation of clause 9, wherein the PLGA-PEG-PLGA has a molecular weight of 1600:1500:1600 Da.

13. The veterinary formulation of clause 9, wherein the PLGA-PEG-PLGA has a molecular weight of 1700-1500-1700 Da.

14. The veterinary formulation of clause 9, wherein the PLGA-PEG-PLGA is a combination of two different PLGA-PEG-PLGA compositions, wherein the first PLGA-PEG-PLGA composition and the second PLGA-PEG-PLGA composition are selected from the group consisting of a PLGA-PEG-PLGA with a molecular weight of 1100:1000:1100 Da, a PLGA-PEG-PLGA with a molecular weight of 1500:1500:1500 Da, a PLGA-PEG-PLGA with a molecular weight of 1600:1500:1600 Da, and a PLGA-PEG-PLGA with a molecular weight of 1700-1500-1700 Da.

15. The veterinary formulation of clause 9, wherein the PLGA-PEG-PLGA is a combination of two different PLGA-PEG-PLGA compositions, wherein the first PLGA-PEG-PLGA composition has a molecular weight of 1100:1000:1100 and the second PLGA-PEG-PLGA composition has a molecular weight of 1500:1500:1500.

16. The veterinary formulation of clause 15, wherein the ratio of the first PLGA-PEG-PLGA composition and the second PLGA-PEG-PLGA composition is about 1:1.

17. The veterinary formulation of clause 15, wherein the ratio of the first PLGA-PEG-PLGA composition and the second PLGA-PEG-PLGA composition is about 2:1.

18. The veterinary formulation of clause 15, wherein the ratio of the first PLGA-PEG-PLGA composition and the second PLGA-PEG-PLGA composition is about 3:1.

19. The veterinary formulation of clause 9, wherein the PLGA-PEG-PLGA is at a ratio of 1:1 (lactide:glycolide).

20. The veterinary formulation of clause 9, wherein the PLGA-PEG-PLGA is at a ratio of 2:1 (lactide:glycolide).

21. The veterinary formulation of clause 9, wherein the PLGA-PEG-PLGA is at a ratio of 3:1 (lactide:glycolide).

22. The veterinary formulation of clause 9, wherein the PLGA-PEG-PLGA is at a ratio of 15:1 (lactide:glycolide).

23. The veterinary formulation of clause 6, wherein the thermogel polymer is P(DL)LA-PEG-P(DL)LA.

24. The veterinary formulation of clause 23, wherein the P(DL)LA-PEG-P(DL)LA has a molecular weight of 1700-1500-1700 Da.

25. The veterinary formulation of clause 6, wherein the thermogel polymer is PLCL-PEG-PLCL.

26. The veterinary formulation of clause 25, wherein the PLCL-PEG-PLCL has a molecular weight of 1700-1500-1700 Da.

27. The veterinary formulation of clause 25, wherein the PLGA-PEG-PLGA is at a ratio of 60:40 CL:LA.

28. The veterinary formulation of clause 6, wherein the thermogel polymer has a gelation set point at a temperature of about 30° C. to about 40° C.

29. The veterinary formulation of clause 6, wherein the thermogel polymer has a gelation set point at a temperature of about 33° C. to about 44° C.

30. The veterinary formulation of clause 6, wherein the thermogel polymer has a gelation set point at a temperature of about 33° C. to about 36° C.

31. The veterinary formulation of clause 6, wherein the thermogel polymer has a gelation set point at a temperature of about 31° C. to about 42° C.

32. The veterinary formulation of clause 6, wherein the thermogel polymer has a gelation set point at a temperature of about 27° C. to about 45° C.

33. The veterinary formulation of any one of clauses 1 to 32, wherein the veterinary formulation further comprises one or more dissolution additives.

34. The veterinary formulation of clause 33, wherein the one or more dissolution additives is selected from the group consisting of N-methylpyrolidinone (NMP), mannitol, and mPEG-P (DL) La.

35. The veterinary formulation of clause 34, wherein the mPEG-P (DL) La is mPEG-P (DL) La (2000-2200 Da).

36. The veterinary formulation of any one of clauses 1 to 35, wherein the veterinary formulation is single-use formulation.

37. The veterinary formulation of any one of clauses 1 to 35, wherein the veterinary formulation is a multi-use formulation.

38. The veterinary formulation of any one of clauses 1 to 37, wherein the veterinary formulation is a controlled release formulation.

39. The veterinary formulation of clause 38, wherein the controlled release formulation releases voriconazole from veterinary formulation for about 7 days.

40. The veterinary formulation of clause 38, wherein the controlled release formulation releases voriconazole from veterinary formulation for about 10 days.

41. The veterinary formulation of clause 38, wherein the controlled release formulation releases voriconazole from veterinary formulation for about 14 days.

42. The veterinary formulation of clause 38, wherein the controlled release formulation releases voriconazole from veterinary formulation for about 21 days.

43. The veterinary formulation of clause 38, wherein the controlled release formulation releases voriconazole from veterinary formulation for about 28 days.

44. The veterinary formulation of any one of clauses 1 to 44, wherein the veterinary formulation is an injectable formulation.

45. The veterinary formulation of clause 44, wherein the injectable formulation is configured for injection in a subconjunctival space (SCS).

46. The veterinary formulation of clause 45, wherein the SCS is a dorsal bulbar SCS.

47. The veterinary formulation of clause 45, wherein the SCS is a ventral bulbar SCS.

48. A kit comprising i) voriconazole and ii) a polymer.

49. The kit of clause 48, wherein the kit further comprises an alcohol.

50. The kit of clause 49, wherein the alcohol is ethanol.

51. The kit of any one of clauses 48 to 50, wherein the polymer is a thermogel polymer.

52. The kit of clause 51, wherein the thermogel polymer is selected from the group consisting of poly(ethylene glycol) (PEG), poly(propylene glycol) (PPG), poly (N-isopropyl acrylamide) (PNIPAAm), poly(N,N-diethyl acrylamide) (PDEAM), poly(N-ethyl methacrylamide) (PNEMAM), poly(methyl vinyl ether) (PMVE), poly(2-ethoxyethyl vinyl ether) (PEOVE), poly(N-vinyl isobutyramide) (PNVIBAM), poly(N-vinyl n-butyramide) (PNVBAM), poly(N-vinyl caprolactam) (PNVCa), and poly (hydroxypropyl methacrylamide) (HPMA), PLGA-PEG-PLGA, P(DL)LA-PEG-P(DL)LA, and PLCL-PEG-PLCL.

53. The kit of clause 51, wherein the thermogel polymer is a combination of two or more thermogel polymers selected from the group consisting of poly(ethylene glycol) (PEG), poly(propylene glycol) (PPG), poly (N-isopropyl acrylamide) (PNIPAAm), poly(N,N-diethyl acrylamide) (PDEAM), poly(N-ethyl methacrylamide) (PNEMAM), poly(methyl vinyl ether) (PMVE), poly(2-ethoxyethyl vinyl ether) (PEOVE), poly(N-vinyl isobutyramide) (PNVIBAM), poly(N-vinyl n-butyramide) (PNVBAM), poly(N-vinyl caprolactam) (PNVCa), and poly (hydroxypropyl methacrylamide) (HPMA), PLGA-PEG-PLGA, P(DL)LA-PEG-P(DL)LA, and PLCL-PEG-PLCL.

54. The kit of clause 51, wherein the thermogel polymer is PLGA-PEG-PLGA.

55. The kit of clause 54, wherein the PLGA-PEG-PLGA has a molecular weight of 1100:1000:1100 Da.

56. The kit of clause 54, wherein the PLGA-PEG-PLGA has a molecular weight of 1500:1500:1500 Da.

57. The kit of clause 54, wherein the PLGA-PEG-PLGA has a molecular weight of 1600:1500:1600 Da.

58. The kit of clause 54, wherein the PLGA-PEG-PLGA has a molecular weight of 1700-1500-1700 Da.

59. The kit of clause 54, wherein the PLGA-PEG-PLGA is a combination of two different PLGA-PEG-PLGA compositions, wherein the first PLGA-PEG-PLGA composition has a molecular weight of 1100:1000:1100 and the second PLGA-PEG-PLGA composition has a molecular weight of 1500:1500:1500.

60. The kit of clause 59, wherein the ratio of the first PLGA-PEG-PLGA composition and the second PLGA-PEG-PLGA composition is about 1:1.

61. The kit of clause 59, wherein the ratio of the first PLGA-PEG-PLGA composition and the second PLGA-PEG-PLGA composition is about 2:1.

62. The kit of clause 59, wherein the ratio of the first PLGA-PEG-PLGA composition and the second PLGA-PEG-PLGA composition is about 3:1.

63. The kit of clause 54, wherein the PLGA-PEG-PLGA is at a ratio of 1:1 (lactide:glycolide).

64. The kit of clause 54, wherein the PLGA-PEG-PLGA is at a ratio of 2:1 (lactide:glycolide).

65. The kit of clause 54, wherein the PLGA-PEG-PLGA is at a ratio of 3:1 (lactide:glycolide).

66. The kit of clause 54, wherein the PLGA-PEG-PLGA is at a ratio of 15:1 (lactide:glycolide).

67. The kit of clause 51, wherein the thermogel polymer is P(DL)LA-PEG-P(DL)LA.

68. The kit of clause 67, wherein the P(DL)LA-PEG-P(DL)LA has a molecular weight of 1700-1500-1700 Da.

69. The kit of clause 51, wherein the thermogel polymer is PLCL-PEG-PLCL.

70. The kit of clause 69, wherein the PLCL-PEG-PLCL has a molecular weight of 1700-1500-1700 Da.

71. The kit of clause 69, wherein the PLGA-PEG-PLGA is at a ratio of 60:40 CL:LA.

72. The kit of clause 51, wherein the thermogel polymer has a gelation set point at a temperature of about 30° C. to about 40° C.

73. The kit of clause 51, wherein the thermogel polymer has a gelation set point at a temperature of about 33° C. to about 44° C.

74. The kit of clause 51, wherein the thermogel polymer has a gelation set point at a temperature of about 33° C. to about 36° C.

75. The kit of clause 51, wherein the thermogel polymer has a gelation set point at a temperature of about 31° C. to about 42° C.

76. The kit of clause 51, wherein the thermogel polymer has a gelation set point at a temperature of about 27° C. to about 45° C.

77. The kit of any one of clauses 48 to 76, wherein the kit further comprises one or more dissolution additives.

78. The kit of clause 77, wherein the one or more dissolution additives is selected from the group consisting of N-methylpyrolidinone (NMP), mannitol, and mPEG-P (DL) La.

79. The kit of clause 78, wherein the mPEG-P (DL) La is mPEG-P (DL) La (2000-2200 Da).

80. The kit of any one of clauses 48 to 79, wherein the polymer is a liquid.

81. The kit of clause 80, wherein the liquid polymer is configured to form a gel deposit upon administration to an animal.

82. The kit of clause 81, wherein the gel deposit is formed at a temperature of about 30° C. to about 40° C.

83. The kit of clause 81, wherein the gel deposit is formed at a temperature of about 33° C. to about 44° C.

84. The kit of clause 81, wherein the gel deposit is formed at a temperature of about 33° C. to about 36° C.

85. The kit of clause 81, wherein the gel deposit is formed at a temperature of about 31° C. to about 42° C.

86. The kit of clause 81, wherein the gel deposit is formed at a temperature of about 27° C. to about 45° C.

87. The kit of any one of clauses 48 to 86, wherein the kit further comprises instructions for combination of the voriconazole and the polymer.

88. A method of treating a fungal infection in an animal, said method comprising the step of administering a veterinary formulation comprising i) a therapeutically effective amount of voriconazole and ii) a polymer to the animal.

89. The method of clause 88, wherein the veterinary formulation is the veterinary formulation of any one of clauses 1-47.

90. The method of clause 88, wherein the veterinary formulation is formed from the kit of any one of clauses 48-87.

91. The method of any one of clauses 88-90, wherein the fungal infection is caused by an *Aspergillus* species.

92. The method of any one of clauses 88-90, wherein the fungal infection is caused by a *Fusarium* species.

93. The method of any one of clauses 88-90, wherein the fungal infection is caused by a *Penicillium* species.

94. The method of any one of clauses 88-90, wherein the fungal infection is caused by a *Candida* species.

95. The method of any one of clauses 88-94, wherein the fungal infection is an ocular infection.

96. The method of any one of clauses 88-95, wherein the fungal infection causes keratomycosis in the animal.

97. The method of any one of clauses 88-96, wherein the animal is an equine.

98. The method of clause 97, wherein the equine is a horse.

99. The method of clause 97, wherein the equine is a donkey.

100. The method of clause 97, wherein the equine is a zebra.

101. The method of any one of clauses 88-90, wherein the animal is a feline.

102. The method of any one of clauses 88-90, wherein the animal is a canine.

103. The method of any one of clauses 88-90, wherein the animal is a camelid.

104. The method of clause 103, wherein the camelid is selected from the group consisting of dromedary camels, Bactrian camels, wild Bactrian camels, llamas, alpacas, vicuñas, and guanacos.

105. The method of clause 103, wherein the camelid is a llama.

106. The method of clause 103, wherein the camelid is an alpaca.

107. The method of any one of clauses 88-106, wherein the administration is an injection.

108. The method of clause 107, wherein upon the injection to the animal, the polymer of the veterinary formulation is a liquid.

109. The method of clause 108, wherein the liquid polymer forms a gel deposit in the animal subsequent to the injection.

110. The method of clause 109, wherein the gel deposit is formed at a temperature of about 30° C. to about 40° C.

111. The method of clause 109, wherein the gel deposit is formed at a temperature of about 33° C. to about 44° C.

112. The method of clause 109, wherein the gel deposit is formed at a temperature of about 33° C. to about 36° C.

113. The method of clause 109, wherein the gel deposit is formed at a temperature of about 31° C. to about 42° C.

114. The method of clause 109, wherein the gel deposit is formed at a temperature of about 27° C. to about 45° C.

115. The method of any one of clauses 107 to 114, wherein the injection is in a subconjunctival space (SCS).

116. The method of clause 115, wherein the SCS is a dorsal bulbar SCS.

117. The method of clause 115, wherein the SCS is a ventral bulbar SCS.

118. The method of any one of clauses 88 to 117, wherein the voriconazole diffuses through a cornea of the animal.

119. The method of any one of clauses 88 to 118, wherein the voriconazole diffuses through a sclera of the animal.

120. The method of any one of clauses 88 to 119, wherein the administration provides a concentration of voriconazole greater than the target minimum inhibitory concentration for about 7 days.

121. The method of any one of clauses 88 to 119, wherein the administration provides a concentration of voriconazole greater than the target minimum inhibitory concentration for about 10 days.

122. The method of any one of clauses 88 to 119, wherein the administration provides a concentration of voriconazole greater than the target minimum inhibitory concentration for about 14 days.

123. The method of any one of clauses 88 to 119, wherein the administration provides a concentration of voriconazole greater than the target minimum inhibitory concentration for about 16 days.

124. The method of any one of clauses 88 to 119, wherein the administration provides a concentration of voriconazole greater than the target minimum inhibitory concentration for about 21 days.

125. The method of any one of clauses 88 to 119, wherein the administration provides a concentration of voriconazole greater than the target minimum inhibitory concentration for about 28 days.

126. The method of any one of clauses 88 to 125, wherein the veterinary formulation is administered as a single unit dose.

127. The method of any one of clauses 88 to 125, wherein the veterinary formulation is administered as a multiple dose regimen.

128. The method of any one of clauses 88 to 127, wherein the method further comprises administration of a second therapeutic agent.

129. The method of clause 128, wherein the second therapeutic agent is selected from the group consisting of an oral antifungal agent, an anti-inflammatory agent, and an antibiotic.

130. The method of any one of clauses 88 to 129, wherein the method of treating is performed without co-administration of a topical antifungal to the animal.

131. The method of any one of clauses 88 to 130, wherein the therapeutically effective amount of the voriconazole is at a dose of about 1 mg.

132. The method of any one of clauses 88 to 130, wherein the therapeutically effective amount of the voriconazole is at a dose of about 2 mg.

133. The method of any one of clauses 88 to 130, wherein the therapeutically effective amount of the voriconazole is at a dose of about 2.5 mg.

134. The method of any one of clauses 88 to 130, wherein the therapeutically effective amount of the voriconazole is at a dose of about 3 mg.

135. The method of any one of clauses 88 to 130, wherein the therapeutically effective amount of the voriconazole is at a dose of about 4 mg.

136. The method of any one of clauses 88 to 130, wherein the therapeutically effective amount of the voriconazole is at a dose of about 5 mg.

137. The method of any one of clauses 88 to 130, wherein the therapeutically effective amount of the voriconazole is at a dose of about 7.5 mg.

138. The method of any one of clauses 88 to 130, wherein the therapeutically effective amount of the voriconazole is at a dose of about 10 mg.

139. The method of any one of clauses 88 to 130, wherein the therapeutically effective amount of the voriconazole is at a dose of about 0.001 to about 1 mg/kg of weight of the animal.

140. The method of any one of clauses 88 to 130, wherein the therapeutically effective amount of the voriconazole is at a dose of about 0.01 to about 0.1 mg/kg of weight of the animal.

141. The method of any one of clauses 88 to 130, wherein the voriconazole is released from the polymer at a rate between about 100 µg/day to about 10,000 µg/day.

BRIEF DESCRIPTION OF THE DRAWINGS

FIG. 6A shows schematic depiction of conversion of thermogel with a gelation set point of 32-36° C. from its liquid state to its solid state following SCS injection. FIG. 6B shows a photograph of injection of a 1:1 mixture of PLGA-PEG-PLGA (MW 1100:1000:1100) and PLGA-PEG-PLGA (MW 1500:1500:1500) into the dorsal bulbar SCS of a horse under general anesthesia. FIG. 6C shows dissection of the bulbar conjunctiva to show the thermogel deposit within the dorsal bulbar SCS.

FIG. 7A shows voriconazole release from PLGA-PEG-PLGA (MW 1100:1000:1100). Release rate was greater for voriconazole in crystal form (right line; Thermogel 1) than in ethanol solution (left line; Thermogel 2). FIG. 7B shows voriconazole release from a 1:1 mixture of PLGA-PEG-PLGA (MW 1100:1000:1100) and PLGA-PEG-PLGA (MW 1500:1500:1500).

FIG. 10A shows glass vials containing test samples and PBS were maintained at 34.5° C. in a water bath. FIG. 10B shows samples that were allowed to gel. FIG. 10C shows 1 ml PBS was added to each glass vial. PBS was removed for HPLC analysis and fresh PBS replaced daily.

FIG. 11A shows results at 4° C. and FIG. 11B shows results at 34.5° C. All thermogel samples retained their thermosensitive properties after addition of voriconazole (Groups 2-5). The thermogel retained its thermosensitive properties following combination with voriconazole alone, voriconazole in ethanol solution and methylene blue.

FIG. 15A shows Group on 1 day 1. FIG. 15B shows Group 3 on day 1. FIG. 15C shows Group 1 on day 28. FIG. 15D shows Group 3 on day 28.

FIG. 18A shows identification via visual inspection. FIG. 18B shows visual inspection following freezing with liquid nitrogen and sectioning. FIGS. 18C & 18D show 50 MHz ultrasound examination.

FIG. 20A: Cornea (10×). FIG. 20B: Ciliary body, iris, limbus (2×). FIG. 20C: Conjunctiva (10×). FIG. 20D: Retina (40×). No evidence of inflammation or tissue damaged was observed on histopathologic examination of either eye following injection of the thermogel.

Figure 1A:
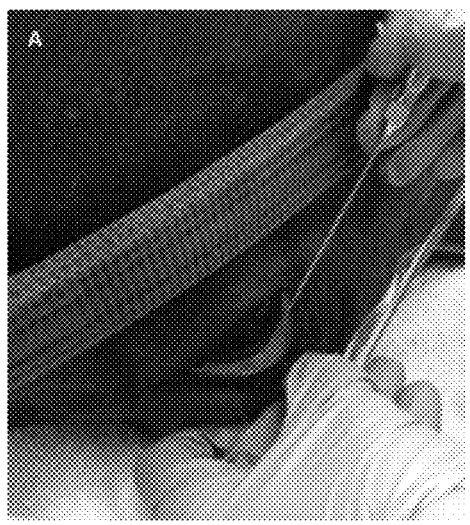
FIGS. 1A-1B show measurement of the temperature in the dorsal bulbar subconjunctival space (FIG. 1A) and ventral bulbar subconjunctival space (FIG. 1B) of a horse under general anesthesia using a Type T thermocouple.

Various embodiments of the invention are described herein as follows. In one embodiment described herein, a veterinary formulation is provided. The veterinary formulation comprises i) a therapeutically effective amount of voriconazole and ii) a polymer.

In another embodiment, a kit is provided. The kit comprises i) voriconazole and ii) a polymer.

In yet another embodiment, a method of treating fungal infection in an animal is provided. The method comprises the step of administering a veterinary formulation comprising i) a therapeutically effective amount of voriconazole and ii) a polymer to the animal.

In various embodiments, the veterinary formulation comprises a therapeutically effective amount of voriconazole. Voriconazole is generally known in the art as an azole antifungal agent and can be used to treat a number of fungal infections, including, for example, aspergillosis, candidiasis, coccidioidomycosis, histoplasmosis, penicilliosis, and infections caused by *Scedosporium* and *Fusarium*.

As used herein, the term "voriconazole" refers to voriconazole base, pharmaceutically acceptable salts of voriconazole, other salts of voriconazole, metabolites of voriconazole, and prodrugs of voriconazole. The term "pharmaceutically acceptable salt" refers to an addition salt that exists in conjunction with the acidic or basic portion of voriconazole. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when voriconazole and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when voriconazole and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

The chemical structure of voriconazole is:

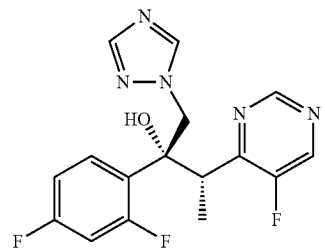 [SMILES: C[C@@H](c1ncncc1F)[C@](O)(Cn1cncn1)c1ccc(F)cc1F]

In the various embodiments, the voriconazole is present in the veterinary formulation at a therapeutically effective amount. As used herein, the term "therapeutically effective amount" refers to an amount which gives the desired benefit to an animal and includes both treatment and prophylactic administration. The amount will vary from one animal to another and will depend upon a number of factors, including the overall physical condition of the animal. The amount of voriconazole used for the therapeutically effective amount gives an acceptable effect and maintains desired response at a beneficial level. A therapeutically effective amount of the composition used in the methods of the present disclosure may be readily ascertained by one of ordinary skill in the art using publicly available materials and procedures.

In certain embodiments, the veterinary formulation further comprises an alcohol. In some embodiments, the alcohol is ethanol.

In various embodiments, the veterinary formulation comprises one or more second therapeutic agents. In some embodiments, second therapeutic agent is selected from the group consisting of an oral antifungal agent, an anti-inflammatory agent, and an antibiotic.

In various embodiments, the polymer is a thermogel polymer. Thermogel polymers (aka "thermogels") are generally known in the art as polymers that exist in liquid phase when refrigerated and exist in solid phase when at room temperature. Typically, the steric hindrance of thermogel polymers combined with a low molecular weight prevents crystallization, and therefore provides their thermosensitivity. Thermogel polymers, when mixed together, provide various ranges in degradation time.

In some embodiments, the thermogel polymer is selected from the group consisting of poly(ethylene glycol) (PEG), poly(propylene glycol) (PPG), poly (N-isopropyl acrylamide) (PNIPAAm), poly(N,N-diethyl acrylamide) (PDEAM), poly(N-ethyl methacrylamide) (PNEMAM), poly(methyl vinyl ether) (PMVE), poly(2-ethoxyethyl vinyl ether) (PEOVE), poly(N-vinyl isobutyramide) (PNVIBAM), poly (N-vinyl n-butyramide) (PNVBAM), poly(N-vinyl caprolactam) (PNVCa), and poly (hydroxypropyl methacrylamide) (HPMA), poly(lactide-co-glycolide)-b-poly(ethylene glycol)-b-poly(lactide-co-glycolide) (PLGA-PEG-PLGA), poly(DL-lactide)-b-Poly(ethylene glycol)-b-Poly(DL-lactide) (P(DL)LA-PEG-P(DL)LA), and poly(lactide-co-caprolactone)-b-Poly(ethylene glycol)-b-Poly(lactide-co-caprolactone) (PLCL-PEG-PLCL).

In other embodiments, the thermogel polymer is a combination of two or more thermogel polymers selected from the group consisting of poly(ethylene glycol) (PEG), poly (propylene glycol) (PPG), poly (N-isopropyl acrylamide) (PNIPAAm), poly(N,N-diethyl acrylamide) (PDEAM), poly (N-ethyl methacrylamide) (PNEMAM), poly(methyl vinyl ether) (PMVE), poly(2-ethoxyethyl vinyl ether) (PEOVE), poly(N-vinyl isobutyramide) (PNVIBAM), poly(N-vinyl n-butyramide) (PNVBAM), poly(N-vinyl caprolactam) (PNVCa), and poly (hydroxypropyl methacrylamide) (HPMA), poly(lactide-co-glycolide)-b-poly(ethylene glycol)-b-poly(lactide-co-glycolide) (PLGA-PEG-PLGA), poly(DL-lactide)-b-Poly(ethylene glycol)-b-Poly(DL-lactide) (P(DL)LA-PEG-P(DL)LA), and poly(lactide-co-caprolactone)-b-Poly(ethylene glycol)-b-Poly(lactide-co-caprolactone) (PLCL-PEG-PLCL).

In certain embodiments, the thermogel polymer is poly (lactide-co-glycolide)-b-poly(ethylene glycol)-b-poly(lactide-co-glycolide) (aka "PLGA-PEG-PLGA"). The structure of PLGA-PEG-PLGA is as follows:

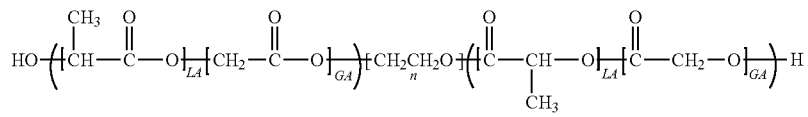

In some embodiments, the PLGA-PEG-PLGA has a molecular weight of 1100:1000:1100. For example, a PLGA-PEG-PLGA with a molecular weight of 1100:1000:1100 can be referred to as PolyVivo AK24 (i.e., Poly(lactic-co-glycolic acid)-b-Poly(ethylene glycol)-b-Poly(lactic-co-glycolic acid) copolymers, with a molecular weight of components at a ratio of 1100:1000:1100 Da and 3:1 lactide:glycolide; Akina, Inc., West Lafayette, Ind.).

In other embodiments, the PLGA-PEG-PLGA has a molecular weight of 1500:1500:1500. For example, a PLGA-PEG-PLGA with a molecular weight of 1500:1500:1500 can be referred to as PolyVivo AK19 (i.e., Poly(lactic-co-glycolic acid)-b-Poly(ethylene glycol)-b-Poly(lactic-co-glycolic acid) copolymers, with a molecular weight of components at a ratio of 1500:1500:1500 Da and 1:1 lactide:glycolide; Akina, Inc., West Lafayette, Ind.).

In yet other embodiments, the PLGA-PEG-PLGA has a molecular weight of 1600:1500:1600 Da. For example, a PLGA-PEG-PLGA with a molecular weight of 1600:1500:1600 can be referred to as PolyVivo AK088 (i.e., Poly (lactic-co-glycolic acid)-b-Poly(ethylene glycol)-b-Poly (lactic-co-glycolic acid) copolymers, with a molecular weight of components at a ratio of 1600:1500:1600 Da and LG 75:25; Akina, Inc., West Lafayette, Ind.).

In other embodiments, the PLGA-PEG-PLGA has a molecular weight of 1700-1500-1700 Da. For example, a PLGA-PEG-PLGA with a molecular weight of 1700-1500-1700 can be referred to as PolyVivo AK097 (i.e., Poly (lactic-co-glycolic acid)-b-Poly(ethylene glycol)-b-Poly (lactic-co-glycolic acid) copolymers, with a molecular weight of components at a ratio of 1700-1500-1700 Da and LA:GA 15:1; Akina, Inc., West Lafayette, Ind.).

In some embodiments, the PLGA-PEG-PLGA is a combination of two different PLGA-PEG-PLGA compositions, wherein the first PLGA-PEG-PLGA composition and the second PLGA-PEG-PLGA composition are selected from the group consisting of a PLGA-PEG-PLGA with a molecular weight of 1100:1000:1100 Da, a PLGA-PEG-PLGA with a molecular weight of 1500:1500:1500 Da, a PLGA-PEG-PLGA with a molecular weight of 1600:1500:1600 Da, and a PLGA-PEG-PLGA with a molecular weight of 1700-1500-1700 Da.

In other embodiments, the PLGA-PEG-PLGA is a combination of two different PLGA-PEG-PLGA compositions, wherein the first PLGA-PEG-PLGA composition has a molecular weight of 1100:1000:1100 and the second PLGA-PEG-PLGA composition has a molecular weight of 1500:1500:1500. In certain aspects, the ratio of the first PLGA-PEG-PLGA composition and the second PLGA-PEG-PLGA composition is about 1:1. In other aspects, the ratio of the first PLGA-PEG-PLGA composition and the second PLGA-PEG-PLGA composition is about 2:1. In other aspects, the ratio of the first PLGA-PEG-PLGA composition and the second PLGA-PEG-PLGA composition is about 3:1.

In yet other embodiments, the PLGA-PEG-PLGA is at a ratio of 1:1 (lactide:glycolide). In some embodiments, the PLGA-PEG-PLGA is at a ratio of 2:1 (lactide:glycolide). In other embodiments, the PLGA-PEG-PLGA is at a ratio of 3:1 (lactide:glycolide). In yet other embodiments, the PLGA-PEG-PLGA is at a ratio of 15:1 (lactide:glycolide).

In certain embodiments, the thermogel polymer is poly (DL-lactide)-b-Poly(ethylene glycol)-b-Poly(DL-lactide) (aka "P(DL)LA-PEG-P(DL)LA"). The structure of P(DL)LA-PEG-P(DL)LA is as follows:

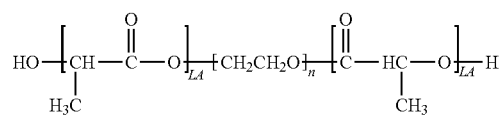

In some embodiments, the P(DL)LA-PEG-P(DL)LA has a molecular weight of 1700-1500-1700. For example, a P(DL)LA-PEG-P(DL)LA with a molecular weight of 1700-1500-1700 can be referred to as PolyVivo AK100 (i.e., Poly(DL-lactide)-b-Poly(ethylene glycol)-b-Poly(DL-lactide) triblock copolymers, with a molecular weight of components at a ratio of 1700-1500-1700 Da; Akina, Inc., West Lafayette, Ind.).

In certain embodiments, the thermogel polymer is poly(lactide-co-caprolactone)-b-Poly(ethylene glycol)-b-Poly(lactide-co-caprolactone) (aka "PLCL-PEG-PLCL"). The structure of PLCL-PEG-PLCL is as follows:

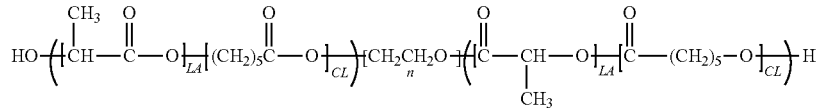

In some embodiments, the PLCL-PEG-PLCL has a molecular weight of 1700-1500-1700. For example, a PLCL-PEG-PLCL with a molecular weight of 1700-1500-1700 can be referred to as PolyVivo AK109 (i.e., Poly(lactide-co-caprolactone)-b-Poly(ethylene glycol)-b-Poly(lactide-co-caprolactone), with a molecular weight of components at a ratio of 1700-1500-1700 Da and 60:40 CL:LA; Akina, Inc., West Lafayette, Ind.).

In various aspects, the thermogel polymer has a gelation set point at a temperature of about 30° C. to about 40° C. As used herein, the gelation set point refers to a temperature or a temperature range at which conversion of a thermogel from its liquid state to its solid state occurs. In other aspects, the thermogel polymer has a gelation set point at a temperature of about 33° C. to about 44° C. In certain aspects, the thermogel polymer has a gelation set point at a temperature of about 33° C. to about 36° C. In other aspects, the thermogel polymer has a gelation set point at a temperature of about 31° C. to about 42° C. In yet other aspects, the thermogel polymer has a gelation set point at a temperature of about 27° C. to about 45° C.

In various embodiments, the veterinary formulation further comprises one or more dissolution additives. Generally, a dissolution additive may be added to the veterinary formulation in order to modify the dissolution speed of the thermogel polymer(s) in the formulation. In some embodiments, the one or more dissolution additives is selected from the group consisting of N-methylpyrolidinone (NMP), mannitol, and mPEG-P (DL) La. In one embodiment, the mPEG-P (DL) La is mPEG-P (DL) La (2000-2200 Da).

In some embodiments, the veterinary formulation is single-use formulation that is intended to be given to an animal in a single administration. In other embodiments, the veterinary formulation is multi-use formulation that is capable of being given to an animal in a single administration or in multiple administrations. Two or more polymers may be combined to achieve the correct temperature for the most efficacious product or for the desired immediate and/or extended release times.

In some embodiments, the veterinary formulation is a controlled release formulation. A controlled release formulation is intended to more slowly release the voriconazole of the veterinary formulation to the animal. In some aspects, the controlled release formulation releases voriconazole from veterinary formulation for about 7 days. In other aspects, the controlled release formulation releases voriconazole from veterinary formulation for about 10 days. In yet other aspects, the controlled release formulation releases voriconazole from veterinary formulation for about 14 days. In some aspects, the controlled release formulation releases voriconazole from veterinary formulation for about 21 days.

In yet other aspects, the controlled release formulation releases voriconazole from veterinary formulation for about 28 days.

In some embodiments, the veterinary formulation is an injectable formulation. As used herein, an injectable formulation refers to a formulation with the ability to be introduced under pressure at a site of an animal (as by introduction using a syringe). "Syringe" refers to any device that may be used to inject or withdraw compositions of the present disclosure. In some aspects, the injectable formulation is configured for injection in a subconjunctival space (SCS) of an animal. As used herein, the subconjunctival space generally refers to the area in an eye of the animal that is located between the conjunctiva and the sclera. In some embodiments, the SCS is a dorsal bulbar SCS. In other embodiments, the SCS is a ventral bulbar SCS.

In another embodiment, a kit is provided. The kit comprises i) voriconazole and ii) a polymer. The previously described embodiments of the veterinary formulation are applicable to the kit described herein.

In various embodiments, the kit further comprises one or more dissolution additives. In some embodiments, the one or more dissolution additives is selected from the group consisting of N-methylpyrolidinone (NMP), mannitol, and mPEG-P (DL) La. In one embodiment, the mPEG-P (DL) La is mPEG-P (DL) La (2000-2200 Da).

In certain aspects, the polymer, for example the polymer provided in the kit, is a liquid. In various embodiments, the liquid polymer is configured to form a gel deposit upon administration to an animal. For example, when the liquid polymer is a thermogel polymer, the liquid polymer undergoes conversion to a gel deposit upon reaching an appropriate temperature.

In some embodiments, the gel deposit is formed at a temperature of about 30° C. to about 40° C. In other embodiments, the gel deposit is formed at a temperature of about 33° C. to about 44° C. In yet other embodiments, the gel deposit is formed at a temperature of about 33° C. to about 36° C. In other embodiments, the gel deposit is formed at a temperature of about 31° C. to about 42° C. In yet other embodiments, the gel deposit is formed at a temperature of about 27° C. to about 45° C.

In certain aspects, the kit further comprises instructions for combination of the voriconazole, the polymer, and any other element as described herein.

In another embodiment, a method of treating a fungal infection in an animal is provided. The method comprises the step of administering a veterinary formulation comprising i) a therapeutically effective amount of voriconazole and ii) a polymer to the animal. The previously described embodiments of the veterinary formulation and of the kit are applicable to the method of treating a fungal infection in an animal described herein. In certain aspects, the veterinary formulation is formed from the kit as described herein.

In various embodiments, the fungal infection is caused by an *Aspergillus* species. In other embodiments, the fungal infection is caused by a *Fusarium* species. In yet other embodiments, the fungal infection is caused by a *Penicil-*

*lium* species. In some embodiments, the fungal infection is caused by a *Candida* species.

In certain aspects, the fungal infection is an ocular infection. In some embodiments, the fungal infection is causes keratomycosis in the animal. Keratomycosis, sometimes referred to as fungal keratitis, is generally known as a fungal infection of the cornea (i.e., the anterior part of the eye which covers the pupil).

In various embodiments, the animal is an equine. In some embodiments, the equine is a horse. In other embodiments, the equine is a donkey. In yet other embodiments, the equine is a zebra.

In some aspects, the animal is a feline. In other aspects, the animal is a canine. In yet other aspects, the animal is a camelid. In some embodiments, the camelid is selected from the group consisting of dromedary camels, Bactrian camels, wild Bactrian camels, llamas, alpacas, vicuñas, and guanacos. In other embodiments, the camelid is a llama. In yet other embodiments, the camelid is an alpaca.

In certain aspects, the administration to the animal is an injection. In some aspects, upon the injection to the animal, the polymer of the veterinary formulation is a liquid. In various aspects, the liquid polymer forms a gel deposit in the animal subsequent to the injection. In some embodiments, the gel deposit is formed at a temperature of about 30° C. to about 40° C. In other embodiments, the gel deposit is formed at a temperature of about 33° C. to about 44° C. In yet other embodiments, the gel deposit is formed at a temperature of about 33° C. to about 36° C. In other embodiments, the gel deposit is formed at a temperature of about 31° C. to about 42° C. In yet other embodiments, the gel deposit is formed at a temperature of about 27° C. to about 45° C.

In some embodiments, the injection is in a subconjunctival space (SCS). In various embodiments, the SCS is a dorsal bulbar SCS. In other embodiments, the SCS is a ventral bulbar SCS.

In certain aspects, the voriconazole diffuses through a cornea of the animal. In other aspects, the voriconazole diffuses through a sclera of the animal.

In some embodiments, the administration provides a concentration of voriconazole greater than the target minimum inhibitory concentration for about 7 days. In other embodiments, the administration provides a concentration of voriconazole greater than the target minimum inhibitory concentration for about 10 days. In yet other embodiments, the administration provides a concentration of voriconazole greater than the target minimum inhibitory concentration for about 14 days. In some embodiments, the administration provides a concentration of voriconazole greater than the target minimum inhibitory concentration for about 16 days. In other embodiments, the administration provides a concentration of voriconazole greater than the target minimum inhibitory concentration for about 21 days. In yet other embodiments, the administration provides a concentration of voriconazole greater than the target minimum inhibitory concentration for about 28 days.

In certain aspects, the veterinary formulation is administered as a single unit dose. In other aspects, the veterinary formulation is administered as a multiple dose regimen. In yet other aspects, the method further comprises administration of a second therapeutic agent. In some embodiments, the second therapeutic agent is selected from the group consisting of an oral antifungal agent, an anti-inflammatory agent, and an antibiotic. In various aspects, the method of treating is performed without co-administration of a topical antifungal to the animal.

In certain embodiments, the therapeutically effective amount of the voriconazole is at a dose of about 1 mg. In some embodiments, the therapeutically effective amount of the voriconazole is at a dose of about 2 mg. In other embodiments, the therapeutically effective amount of the voriconazole is at a dose of about 2.5 mg. In yet other embodiments, the therapeutically effective amount of the voriconazole is at a dose of about 3 mg. In some embodiments, the therapeutically effective amount of the voriconazole is at a dose of about 4 mg. In other embodiments, the therapeutically effective amount of the voriconazole is at a dose of about 5 mg. In yet other embodiments, the therapeutically effective amount of the voriconazole is at a dose of about 7.5 mg. In some embodiments, the therapeutically effective amount of the voriconazole is at a dose of about 10 mg. In other embodiments, the therapeutically effective amount of the voriconazole is at a dose of about 0.001 to about 1 mg/kg of weight of the animal. In yet other embodiments, the therapeutically effective amount of the voriconazole is at a dose of about 0.01 to about 0.1 mg/kg of weight of the animal. In other embodiments, the voriconazole is released from the polymer at a rate between about 100 µg/day to about 10,000 µg/day.

EXAMPLE 1

Equine Bulbar Subconjunctival Space Temperature Determination

Thermogels injected into the subconjunctival space (SCS) can be utilized as a sustained delivery system targeting the cornea and anterior chamber in equines, such as horses. This example describes the bulbar SCS temperature in normal horse eyes in order to identify the optimal gelation temperature set point of thermogels intended for bulbar SCS injection in horses.

Figure 1B:
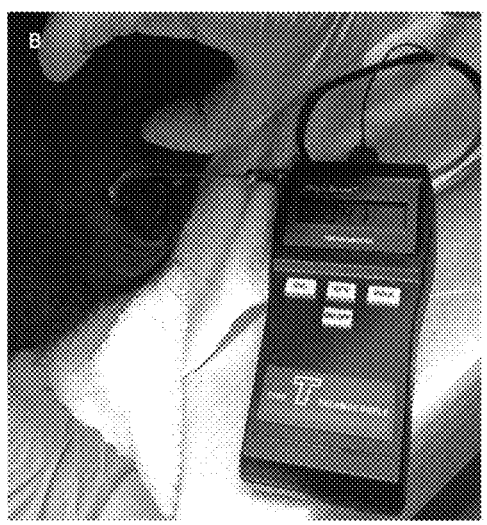

Ten adult horses participating in student surgical laboratories at the AULATH were enrolled in this study. Horses were pre-medicated with xylazine (Anased®, Akom, Inc., Decatur, Ill.) then general anesthesia was induced with ketamine (Ketaset®, Fort Dodge Animal Health, Fort Dodge, Iowa) and maintained via inhalation of isoflurane (Fluriso®, Vet One, Boise, Id.). Temperature measurements were collected within 10 minutes of anesthetic induction. Dorsal and ventral SCS temperatures were measured in the left and right eye using a Type T thermocouple (Cole-Palmer, Vernon Hills, Ill.) (see FIG. 1). Rectal temperatures were measured using an electronic rectal thermometer (Provet, Sydney, NSW). Temperatures in the left and right SCS, the dorsal and ventral SCS and rectal and mean SCS temperatures were compared using paired t-tests. Results were reported as range and mean±standard deviation and significance was set at a value of $P<0.05$.

Horses were of mixed breed (4 Thoroughbreds, 5 Quarter Horses, 1 Trakehner) and gender (3 mares, 6 geldings, 1 stallion). The average age of the horses enrolled in the study was 14.4 years (range: 3-25 years), and their average weight was 466.2 kg (range: 385-444 kg).

Figure 2:
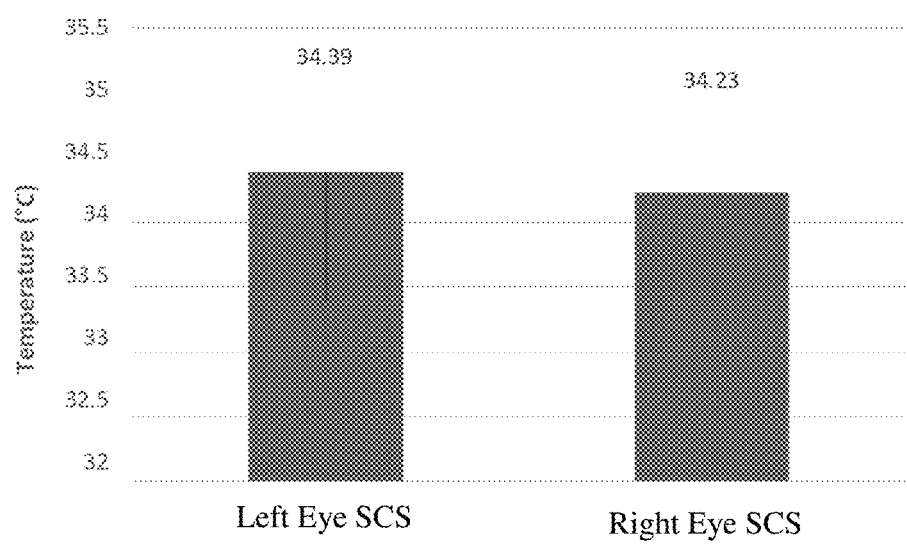
FIG. 2 shows mean temperature±SD (° C.) in the equine bulbar subconjunctival space by location. There was no significant difference between mean temperatures in the SCS of the left and right eyes.
Figure 3:
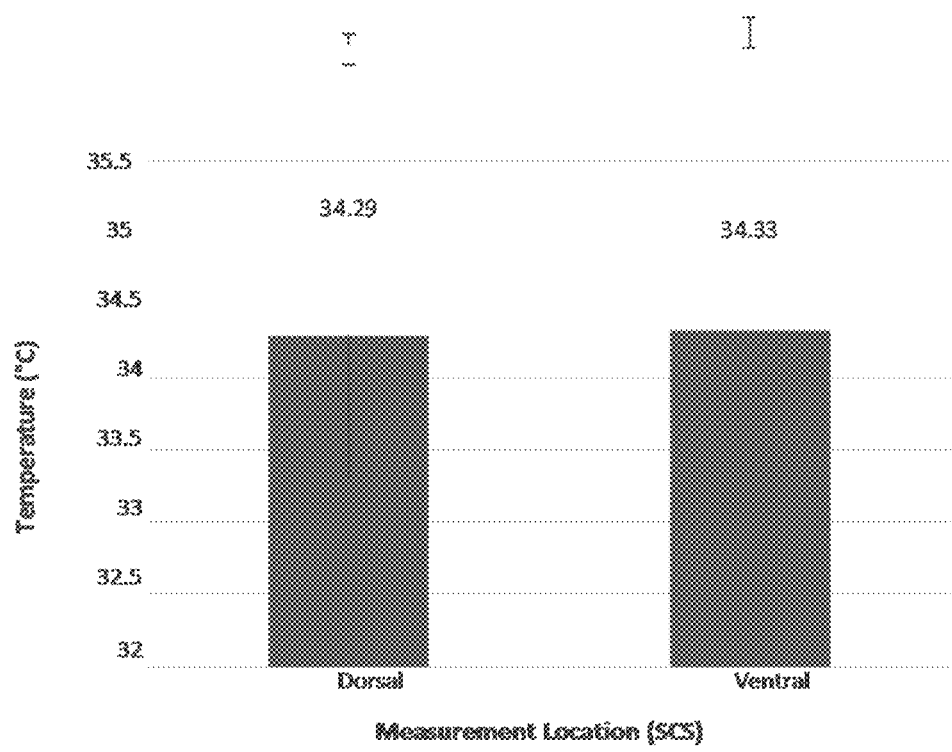
FIG. 3 shows mean temperature±SD (° C.) in the equine bulbar subconjunctival space by location. There was no significant difference between mean temperatures in the dorsal and ventral SCS.

Forty SCS temperature and 10 rectal temperature measurements were recorded. SCS temperatures ranged from 33.3° C.-35.3° C. (34.5° C.±0.6° C.) in the dorsal bulbar SCS and 33.3° C.-35.3° C. (34.5° C.±0.6° C.) in the ventral bulbar SCS. Rectal temperatures ranged from 36.1-38.5° C. (37.3° C.±0.7° C.). There was no significant difference between SCS temperatures in the left and right eye ($P=0.276$) (see FIG. 2) or between temperatures in the dorsal bulbar SCS and the ventral bulbar SCS ($P=0.739$) (see FIG.

Figure 4:
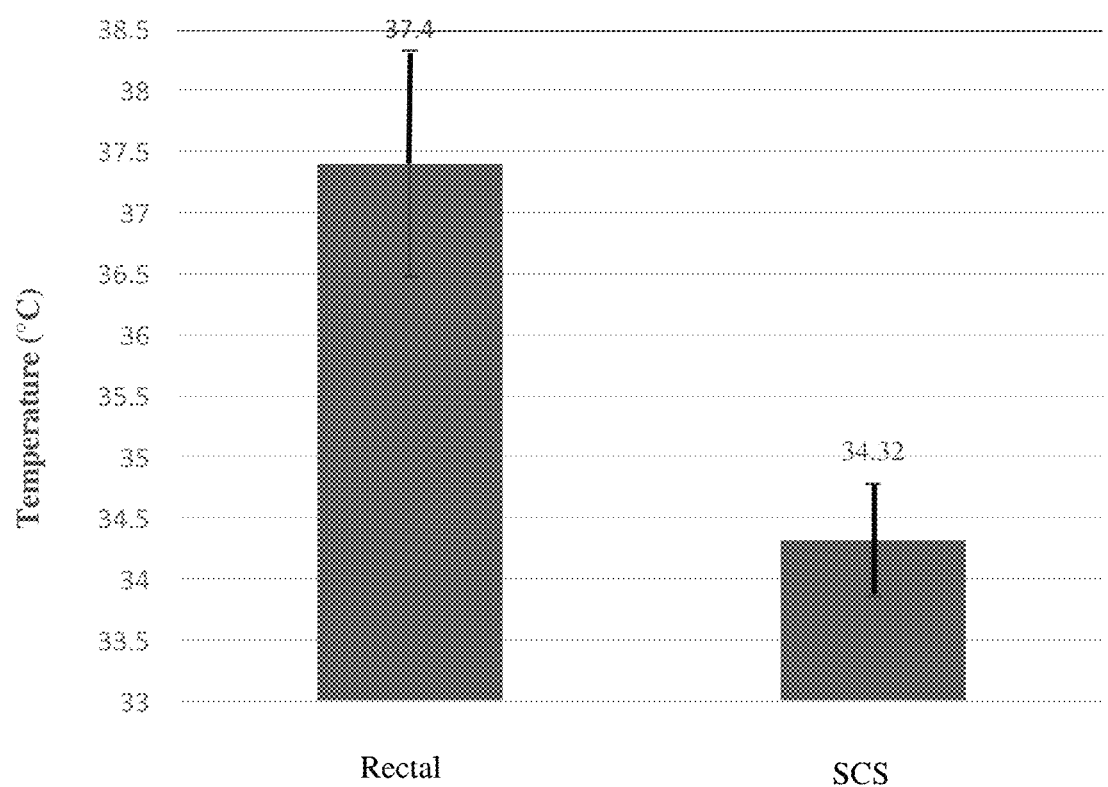
FIG. 4 shows mean rectal and subconjunctival space temperatures±SD (° C.) in anesthetized adult horses. There was a significant difference between rectal and SCS temperatures.

3). There was a significant difference between the temperatures measured in the rectum and the bulbar SCS (P=0.0000001) (see FIG. 4). The temperature difference between rectal and SCS temperatures ranged from 2.0° C.-4.1° C. (2.8° C.; ±0.6° C.).

The mean and range of temperatures in the bulbar SCS of adult horses are 34.5° C. and 33.3° C.-35.3° C. respectively. There is no significant difference between the temperature in the dorsal and ventral bulbar SCS of individual eyes or between the bulbar SCS of contralateral eyes in horses. The mean difference between the rectal and SCS temperature in horses is 2.8° C., however the SCS temperature can range from 2.0° C.-4.1° C. lower than the rectal temperature in horses. The above findings are consistent with previously reported bulbar SCS temperatures in humans and rabbits, when adjusted for species specific core temperature ranges. It may be beneficial for a thermogel for injection in the SCS of horses to have a gelation set point between about 33° C. and about 36° C.

EXAMPLE 2

Thermogel Identification

This example examines various thermogels for the present disclosure. In particular, various PLGA-PEG-PLGA thermogels were evaluated for injection into the SCS in horses and to determine whether or not the gel retained its thermosensitive properties following combination with voriconazole and methylene blue.

Two commercially available PLGA-PEG-PLGA triblock copolymers (AK24/'thermogel A' (MW 1100-1000-1100; 3:1 lactide:glycolide) and AK19/'thermogel B' (MW 1500-1500-1500; 1:1 lactide:glycolide); Akina Inc., West Lafayette, Ind.) were converted from a solid state (−20° C.) to a liquid state through addition of 0.9% sodium chloride (Hospira Inc., Lake Forest, Ill.), vortexing every 8 hours for 48 hours and maintenance at 4° C. Five thermogels were tested: thermogel A, thermogel B and thermogels combined in A:B ratios of 1:1, 2:1 and 3:1.

Each thermogel tested was divided into 4×300 µL aliquots (Groups 1, 2 3 and 4). Group 1 aliquots were placed in glass vials which were placed in a water bath at 21° C. for 30 minutes, stored overnight at 4° C., placed in a water bath at 35° C. for 30 minutes, then again stored at 4° C., and conversions from liquid to solid state reported. Group 2 aliquots were placed in glass vials to which 1 mg voriconazole (U. S. Pharmacopeia, Rockville, Md.) was added, and Group 3 aliquots were placed into glass vials to which 10 µL of methylene blue (Akorn Inc., Lake Forest, Ill.) was added; the vials were maintained at 4° C., vortexed every 8 hours for 48 hours and then subjected to the temperature changes described above. Group 4 aliquots were injected through a 30 gauge needle into the bulbar subconjunctival space of a horse under general anesthesia that was enrolled in a terminal student surgical laboratory at the AULATH.

Figure 5A:
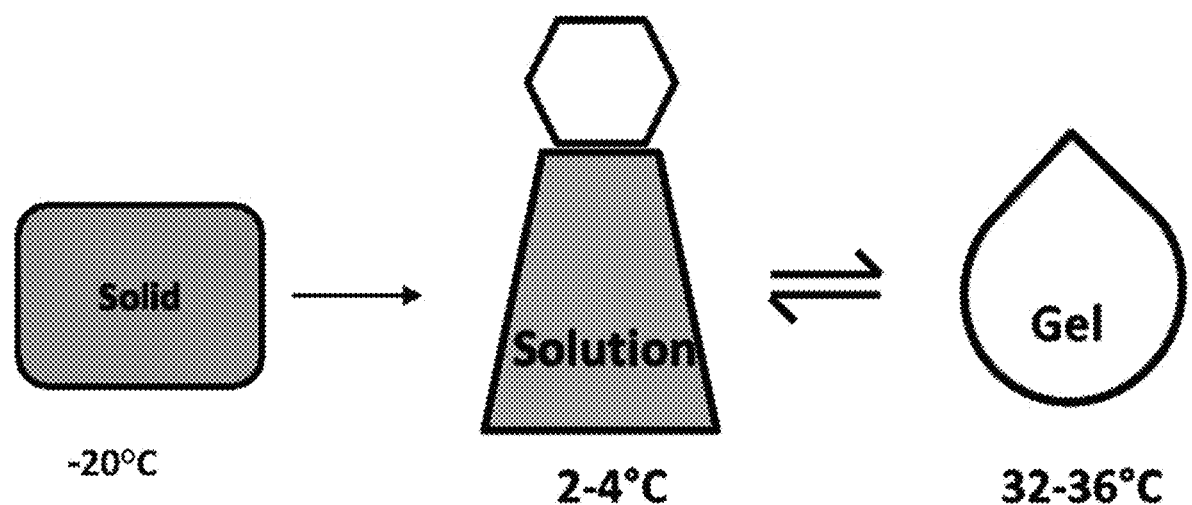
FIGS. 5A-5B show a schematic depiction of conversion of thermogel with a gelation set point of 32-36° C. from its solid to liquid state to gel state (FIG. 5A) and the reversible liquid to gel transition of a thermogel consisting of a 1:1 mixture of PLGA-PEG-PLGA (Mw 1100:1000:1100) and PLGA-PEG-PLGA (Mw 1500:1500:1500) (FIG. 5B).
Figure 5A:
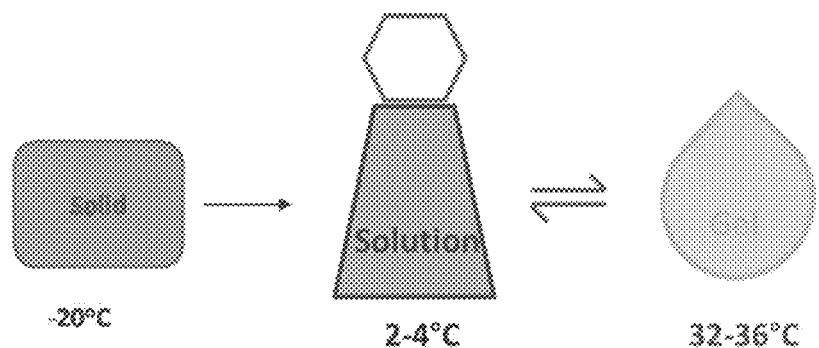
Figure 5B:
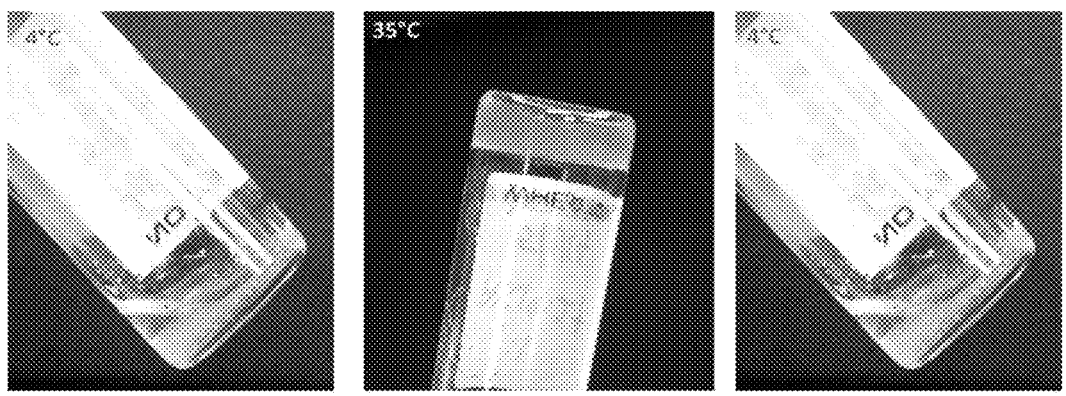

Thermogel A formed a firm gel within 20 seconds at 21° C. but did not gel at 35° C. Thermogel B did not gel at 21° C. but underwent partial gelation at 35° C. Thermogels in A:B ratios of 1:1, 2:1 and 3:1 did not gel at 21° C. but formed firm gels within 30, 45 and 60 seconds respectively at 35° C. (see FIGS. 5A and 5B). All thermogels returned to liquid state when vials were returned to a 4° C. environment. Voriconazole was able to be combined with all five thermogels, and all thermogels retained their thermosensitive characteristics following combination with voriconazole and methylene blue. All thermogels were able to be injected through a 30 gauge needle into the bulbar SCS of a horse under general anesthesia. Thermogel A did not firm a discrete deposit in the SCS.

Figure 6A:
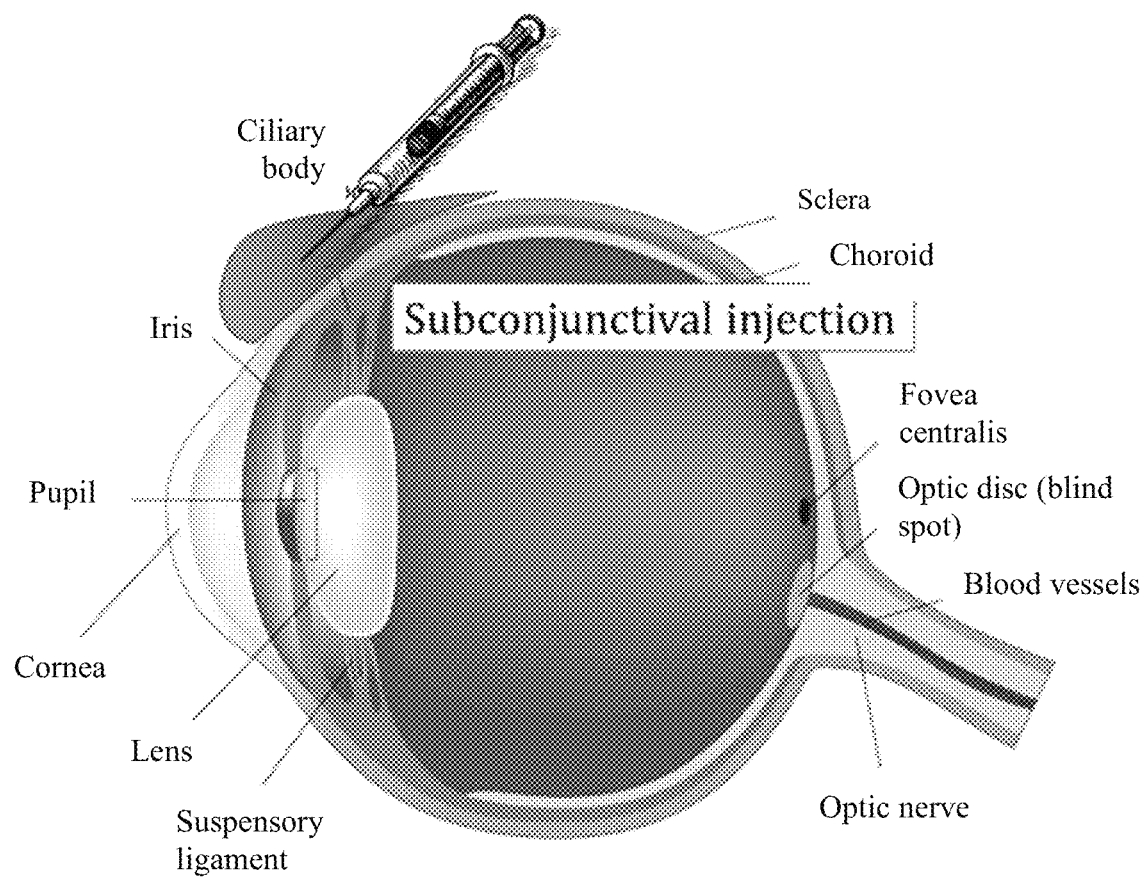
FIGS. 6A-6C.
Figure 6A:
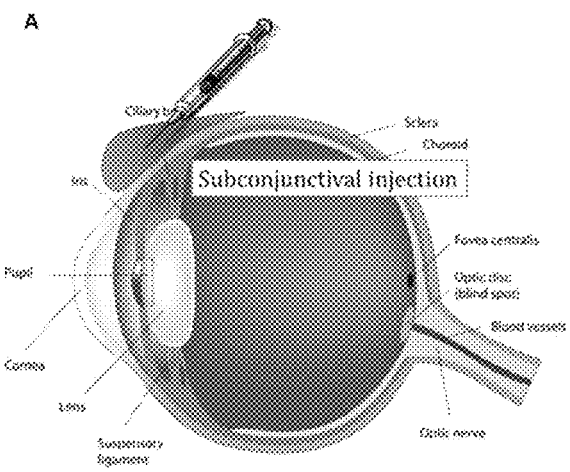
Figure 6B:
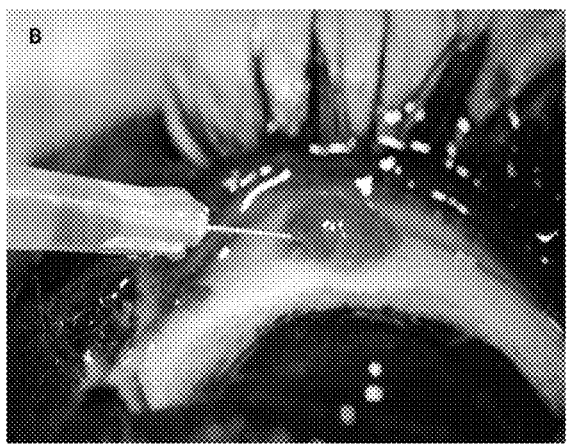
Figure 6C:
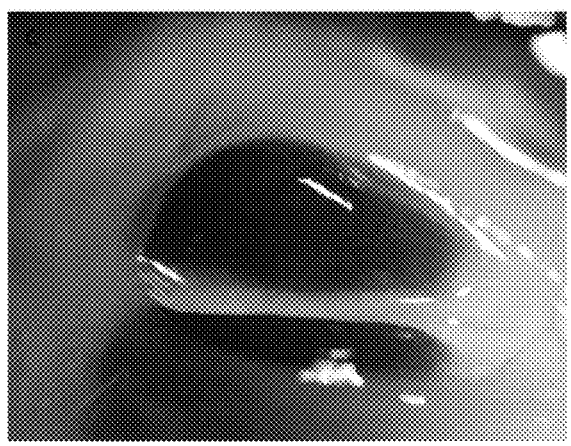

Thermogel B and thermogels with A:B ratio of 2:1 and 3:1 formed soft, poorly-defined deposits in the bulbar SCS. The thermogel with 1:1 A:B ratio formed a firm, discrete gel deposit in the equine bulbar SCS (see FIGS. 6A-6C).

The optimal gelation set points of the thermogels tested were consistent with rheological data. The thermosensitive characteristics of the tested thermogels were not changed by addition of voriconazole or methylene blue. A thermogel with 1:1 ratio of PLGA-PEG-PLGA (1100:1000:1100): PLGA-PEG-PLGA (1500:1500:1500) was selected for further studies of injection in the equine bulbar SCS.

EXAMPLE 3

Voriconazole Release from Thermogels

A voriconazole-containing thermogel for subconjunctival injection can provide for sustained drug release into target tissues. This example describes the solubility of voriconazole in crystalline form and in ethanol solution in a volume of thermogel suitable for SCS injection (300 µl). Various thermogels containing 1 mg voriconazole are evaluated regarding their release of drug in concentrations exceeding the MIC of common equine fungal pathogens (0.5 µg/ml) for at least 7 days in vitro.

Two PLGA-PEG-PLGA hydrogels were converted from a solid state (−20° C.) to a liquid state through addition of 0.9% sodium chloride, vortexing every 8 hours for 48 hours and maintenance at 4° C. Three thermogels were then prepared:

Thermogel 1: 1 mg voriconazole+300 µl PLGA-PEG-PLGA (MW 1100:1000:1100)

Thermogel 2: 1 mg voriconazole in 10 µl ethanol (Sigma-Aldrich, St Louis, Mo.)+300 µl PLGA-PEG-PLGA (MW 1100:1000:1100)

Thermogel 3: 1 mg voriconazole+300 µl 1:1 PLGA-PEG-PLGA (MW 1100:1000:1100):PLGA-PEG-PLGA (MW 1500:1500:1500).

Each thermogel was stored in a glass vial and was maintained at its optimal gelation temperature (23° C. for Thermogels 1 and 2; 35° C. for Thermogel 3) together with 1 ml phosphate buffered saline (PBS) in a water bath for 21 days. Twice daily visual inspection of samples was performed for the 21 days. All PBS was collected daily and replaced with fresh PBS for 14 days and voriconazole content determined via liquid chromatography-tandem mass spectrometry.

Figure 7A:
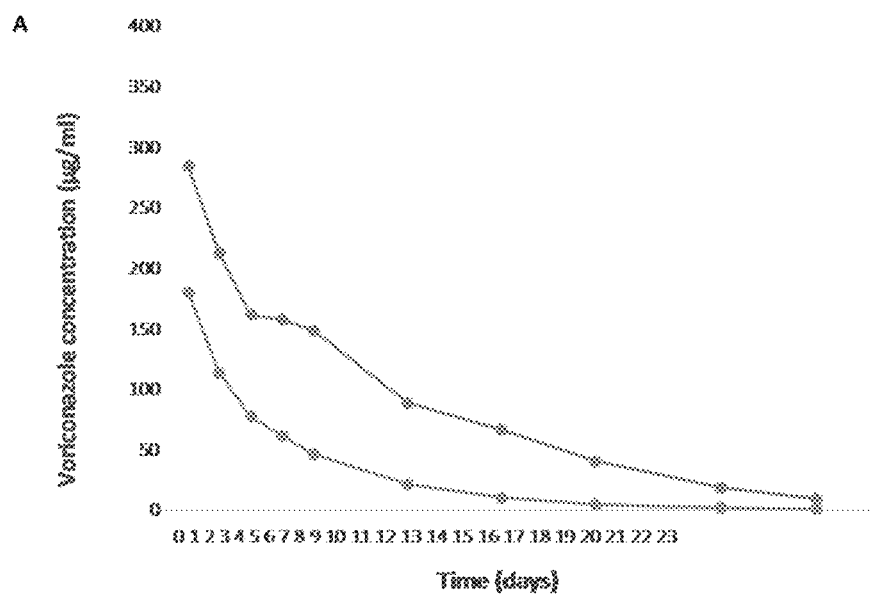
FIGS. 7A-7B.
Figure 7B:
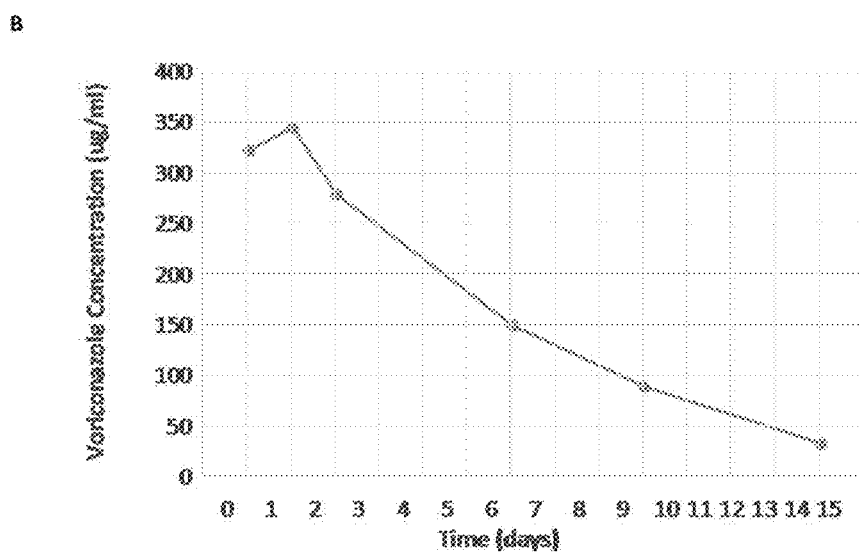

Voriconazole was successfully combined with two PLGA-PEG-PLGA hydrogels in liquid form. Both hydrogels retained their thermosensitive properties when combined with voriconazole in crystalline form and in ethanol solution. Phase separation of the thermogels occurred after 12 hours, with less than a quarter of the thermogel aliquot entering an aqueous phase and the balance remaining a discrete gel. Voriconazole was released from the thermogels over 14 days with concentrations achieved in excess of the target MIC at all time points (see FIGS. 7A and 7B).

Voriconazole is able to be combined with, and is released in a sustained manner from, thermosensitive PLGA-PEG-PLGA thermogels in vitro for at least 14 days. Investigation into solubility of voriconazole at higher concentrations and subsequent in vitro drug release is indicated.

EXAMPLE 4

An Ex-Vivo Trans-Corneal Permeation Model in Horses

Franz cell diffusion studies are utilized in evaluation of permeation of topical ocular medications through human, goat, and sheep corneas. This example describes an ex-vivo trans-corneal drug permeation model for use in equine corneas, and also presents evidence on the integrity of the equine epithelial barrier function for 6 hours.

Figure 8A:
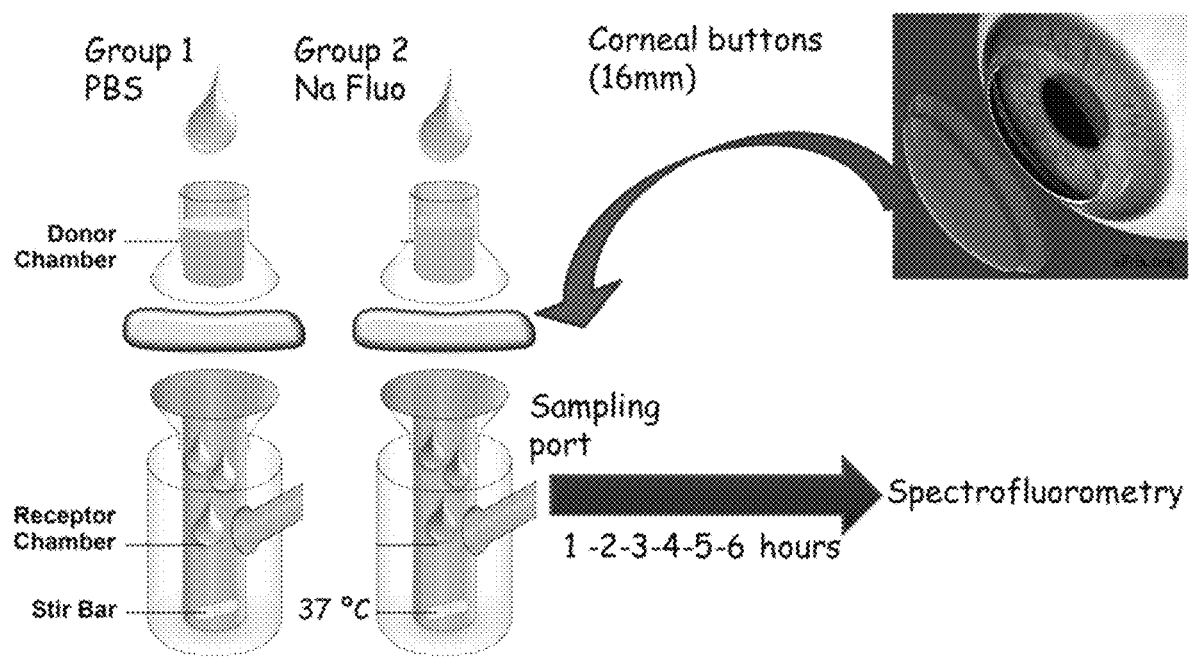
FIGS. 8A-8B show the schematic (FIG. 8A) and photographic (FIG. 8B) depiction of the Franz cell diffusion apparatus used to develop a permeation model for equine corneas.
Figure 8B:

Fresh equine corneas used in the experiment were obtained from horses enrolled in terminal laboratories performed at the AULATH. Corneoscleral buttons (16 mm diameter) were dissected using standard eye bank technique within 2 hours of enucleation. Fluorescent permeation experiments using a Franz diffusion cell method were performed to examine the integrity of the epithelial barrier function during the times studied (2 and 6 hours). Corneas were mounted horizontally between the donor and the receiving compartments of the diffusion cells (exposure window 0.64 $cm^2$), which were maintained at 37° C. (see FIGS. 8A and 8B).

Two test groups were defined: a control group in which the donor compartment was filled with 1 ml PBS pH 7.4 (Group 1) and a fluorescein group in which the donor compartment was filled with 1 ml of a solution containing PBS pH 7.4 and 10 µM sodium fluorescein (NaF) (Group 2).

Samples (1 ml PBS pH 7.4) were removed from the receiving compartment hourly and replaced with fresh receiving fluid. The fluorescent intensities of the receiving solution samples were analyzed using a microplate spectrofluorometer (Fluostar, BMG Labtech, Ortenberg, Germany) and a 96 well plate (Costar, Corning, N.Y.). A standard solution of NaF was prepared in PBS with a concentration range of 30 µg/ml to 0.12 µg/ml. Fluorescence was determined in a spectrofluorometer at excitation and emission wavelengths of 490 nm and 512 nm, respectively. All groups were tested in triplicate. The results were expressed as mean value±standard error of the mean (SEM). The differences between values for Group 1 and Group 2 were assessed using a one-way analysis of variance (ANOVA) ($p<0.05$).

Figure 9:
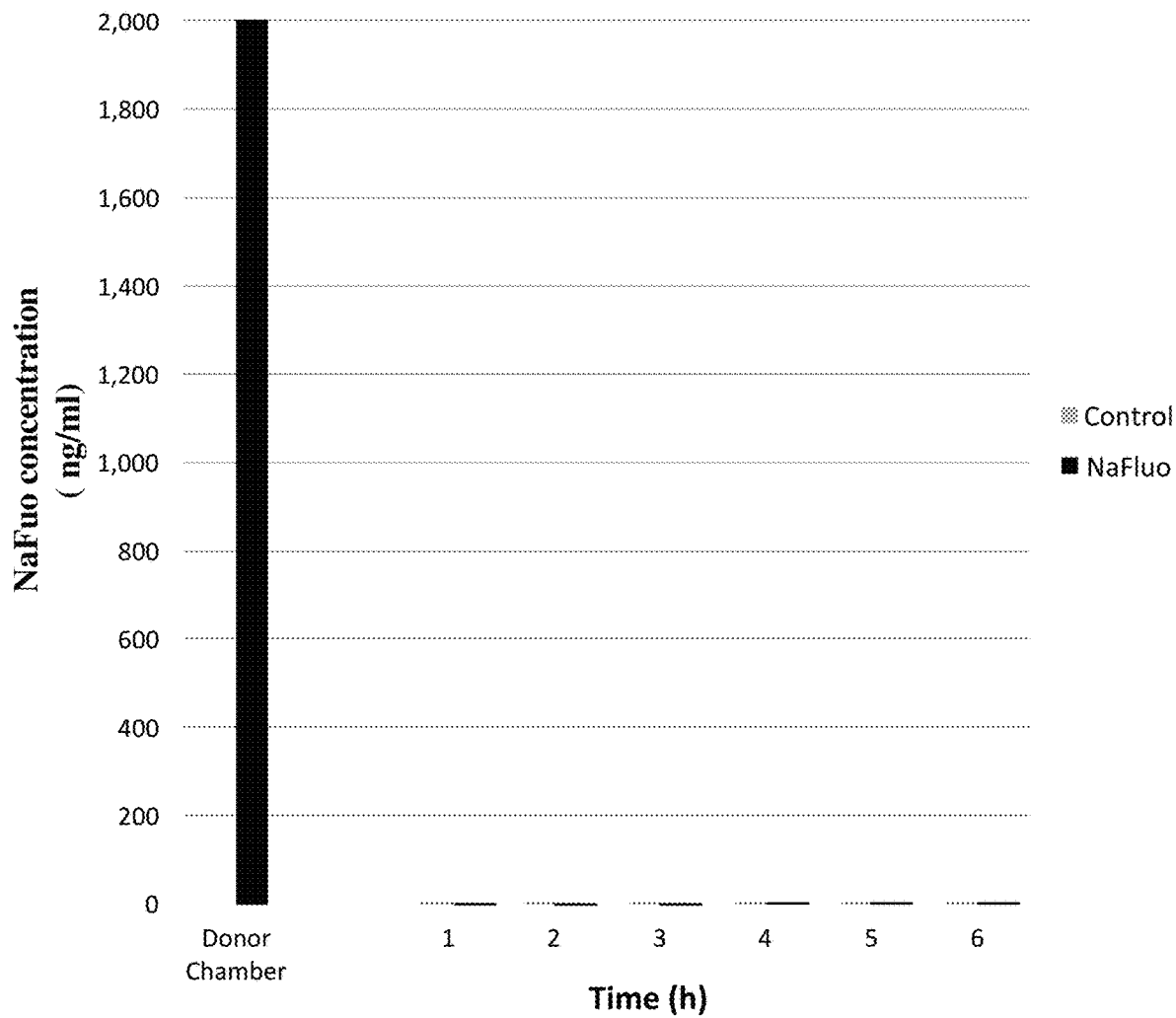
FIG. 9 shows the concentration of fluorescein (NaFluo) measured in the donor chamber and receiving compartment over 6 hours of the in vitro permeation study; mean±SD, n=3. Fluorescent concentrations detected in the receiving compartment were not significantly different than those obtained from the negative control experiment at any time point.

Fluorescent concentrations detected in the receiving compartment of experiments maintained for 2 and 6 hours were not significantly different than those obtained from the negative control experiment at any time point, showing that the epithelial barrier function was maintained (see FIG. 9). The results indicate that the diffusion cell was able to maintain the integrity of equine epithelial corneal barrier function throughout the 6 hours of the permeation experiment.

EXAMPLE 5

In Vitro Release of Voriconazole from a PLGA-PEG-PLGA Thermogel

This example investigates the release of voriconazole from thermogel over a 4 week period. Concentrations of voriconazole released from the thermogels were evaluated and compared to the MIC for common fungal organisms implicated in equine keratomycosis, e.g. *Fusarium*, *Aspergillus*, and *Candida* spp.

Thermogel Preparation

Two commercially available, thermosensitive PLGA-PEG-PLGA triblock copolymers (AK24 (MW 1100-1000-1100; 3:1 lactide:glycolide) and AK19 (MW 1500-1500-1500; 1:1 lactide:glycolide); Akina Inc., West Lafayette, Ind.) were purchased in solid form (−20° C.). Both PLGA-PEG-PLGA thermogels were converted to an aqueous solution via addition of 0.9% sodium chloride (80% w/w; Hospira Inc., Lake Forest, Ill.), vortexing for 1 minute every 8 hours for a period of 48 hours and storage at 4° C. (liquid form). The two thermogel solutions were then combined in a 1:1 ratio to form a thermogel with an optimal gelation set point of 32° C.-36° C. (hereafter referred to as 'the thermogel'), concordant with that of the equine bulbar SCS (average temperature 34.5° C.). Test groups containing different concentrations of voriconazole were prepared as outlined below.

In all cases voriconazole crystals (U. S. Pharmacopeia, Rockville, Md.) or voriconazole in ethanol (Sigma-Aldrich, St. Louis, Mo.) solution were added to the thermogel at 4° C. and the resultant voriconazole-containing thermogel was vortexed for 1 minute every 8 hours for a period of 48 hours to distribute the drug within the thermogel. The thermogel used for ex vivo injection was stained with methylene blue (Akorn Inc., Lake Forest, Ill.) for ease of visualization.

In Vitro Release of Voriconazole from the Thermogel

Six test groups were prepared, five consisting of 300 µl aliquots of the thermogel combined with voriconazole in the following concentrations: 0% (Group 1; negative control group), 0.3% voriconazole (1 mg; Group 2), 0.3% voriconazole (1 mg in ethanol solution; Group 3), 1.5% voriconazole (5 mg; Group 4) and 1.5% voriconazole (5 mg in ethanol solution; Group 5), and one positive control group consisting of voriconazole crystals alone (5 mg; Group 6).

Figure 10A:
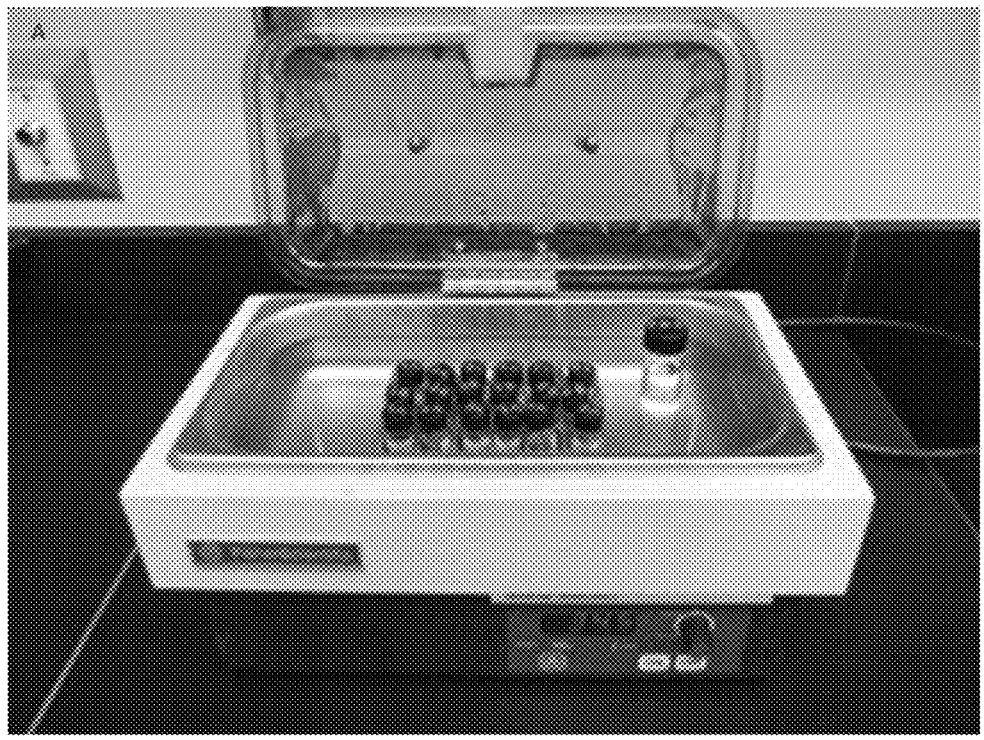
FIGS. 10A-10C show voriconazole release study in which 6 test groups were tested in triplicate.
Figure 10B:
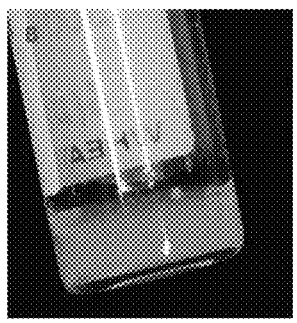
Figure 10C:
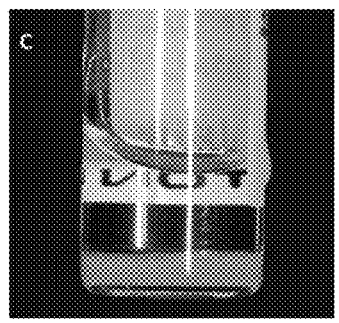

The thermogels were prepared in glass vials at 4° C. (liquid state). Conversion to a gel state was facilitated by suspension of the glass vials in a water bath set at a constant temperature of 34.5° C., where they were maintained for 28 days. Immediately following conversion of the thermogel to a gel state, 1 ml 0.067M PBS (Lonza, Walkersville, Md.) was added to each vial (see FIGS. 10A-10C).

The PBS was collected from the vials and replaced with 1 ml of fresh PBS at each sampling time point. Samples were collected at 6, 12, 18 and 24 hours on day 1, then every 24 hours for a further 27 days. Samples were stored at −80° C. until the end of the testing interval and then analyzed for voriconazole concentration via reverse phase high-performance liquid chromatography (HPLC). Observations of thermogel appearance were recorded daily. Each formulation was tested in triplicate.

Figure 11A:
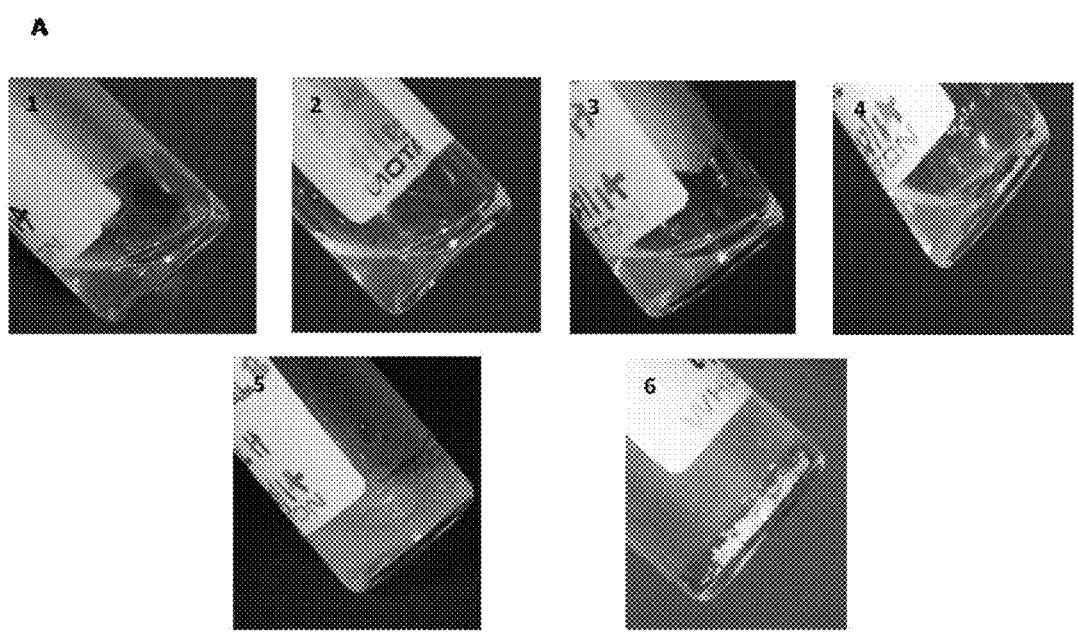
FIGS. 11A-11B show the results of tests groups 1-6.
Figure 11B:
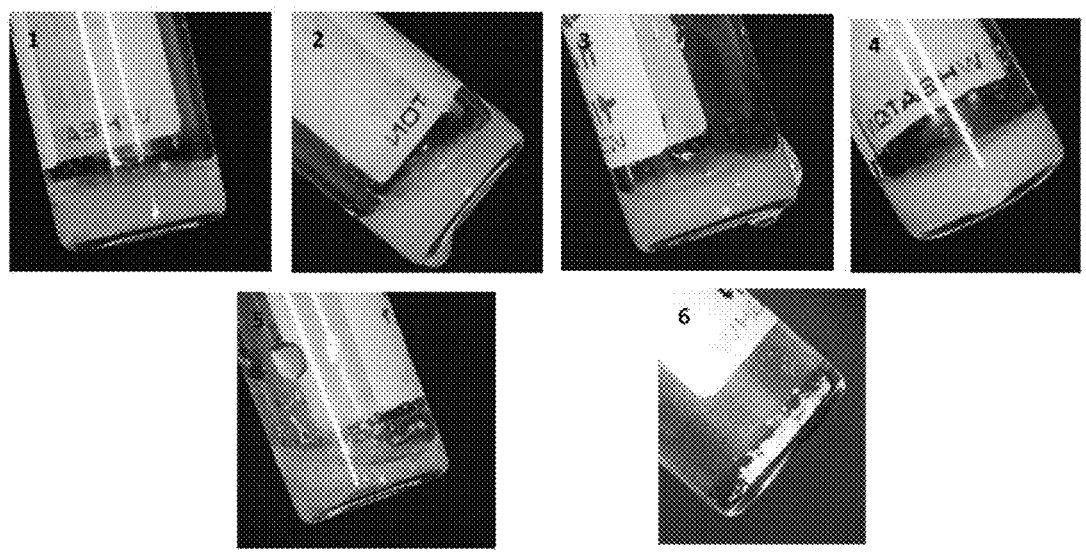

Voriconazole completely dissolved within the thermogel in Groups 2, 3, and 5 to form an aqueous solution (see FIGS. 11A and 11B). Voriconazole dispersed well within the thermogel, forming a suspension, in Group 4. The thermogel retained its thermosensitive properties following combination with voriconazole alone, voriconazole in ethanol solution and methylene blue.

Figure 12:
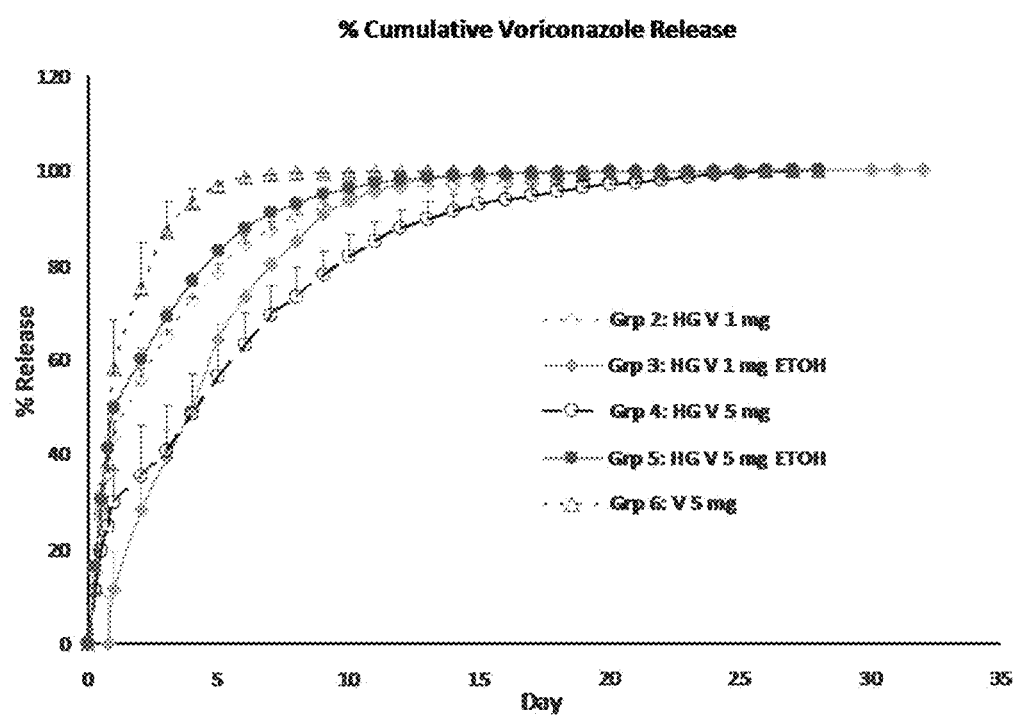
FIG. 12 shows the percentage (%) of cumulative voriconazole release from the thermogels. Voriconazole was sustainably released from the thermogels throughout the study period. Addition of ethanol altered voriconazole release.
Figure 13:
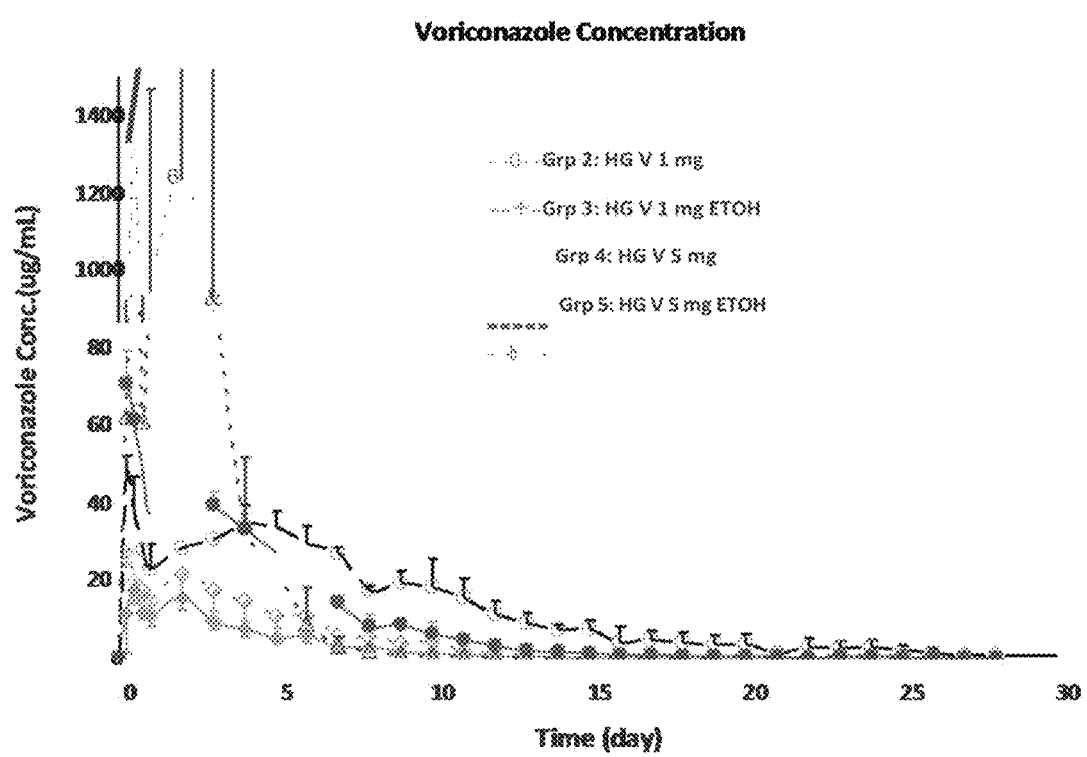
FIG. 13 shows the voriconazole concentration in PBS over time. Voriconazole release exceeded the target MIC (0.5 μg/ml) for 28 days in Groups 2 and 4 and 16 days in Groups 3 and 5.
Figure 14:
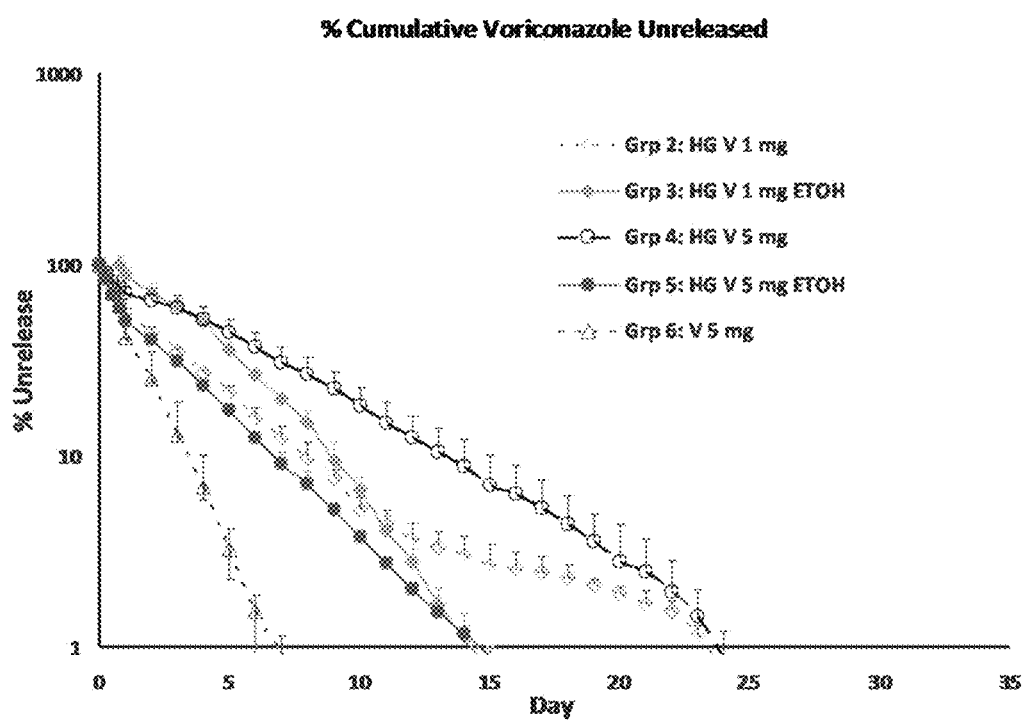
FIG. 14 shows the percentage (%) cumulative voriconazole unreleased from the thermogels over time. Addition of ethanol hastened drug release.
Figures 15A, 15B, 15C, 15D:
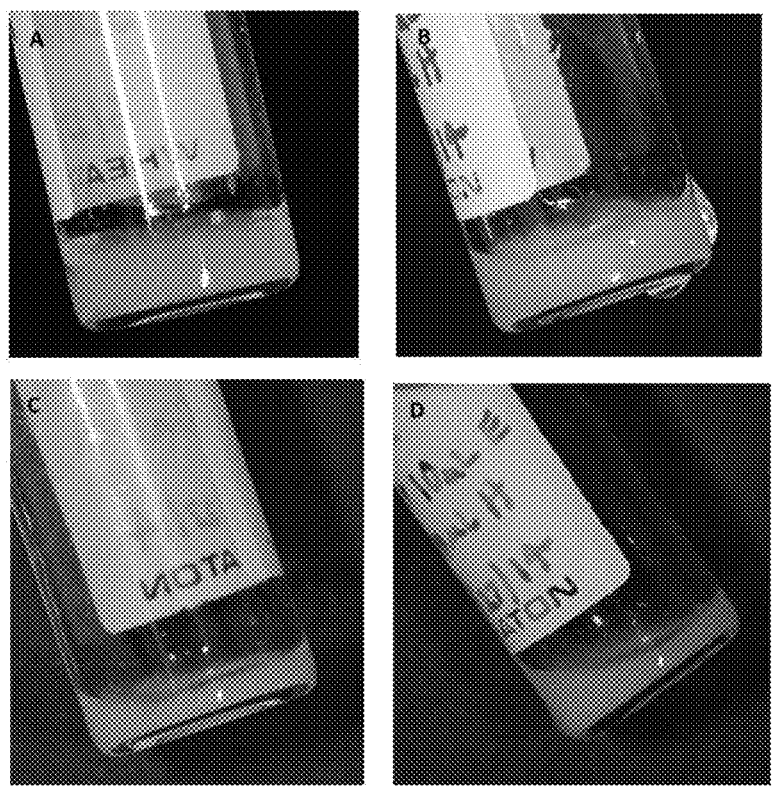
FIGS. 15A-15D show thermogel degradation over time. Addition of ethanol slowed the degradation of the thermogel, in which more thermogel remaining in Groups 3 and 5 than Groups 1, 2, and 4 at study completion.
Figures 16A, 16B:
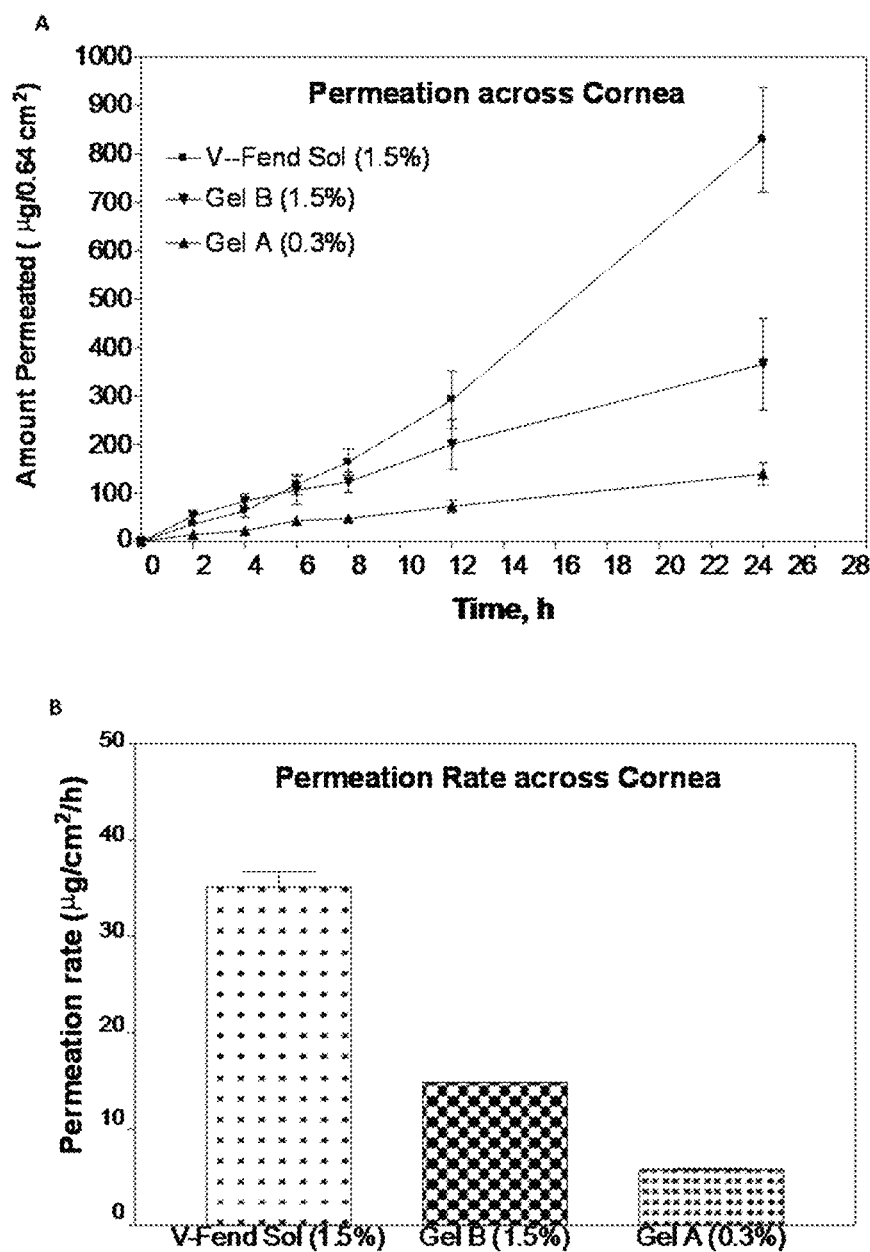
FIGS. 16A-16B show the permeation of voriconazole across the cornea over time (FIG. 16A) and the permeation rate across the cornea (FIG. 16B). A concentration dependent increase in the permeation of voriconazole from the thermogel formulations was noted. Gel B (1.5% voriconazole-thermogel) showed significantly lower permeation as compared to the 1.5% voriconazole solution.
Figures 17A, 17B:
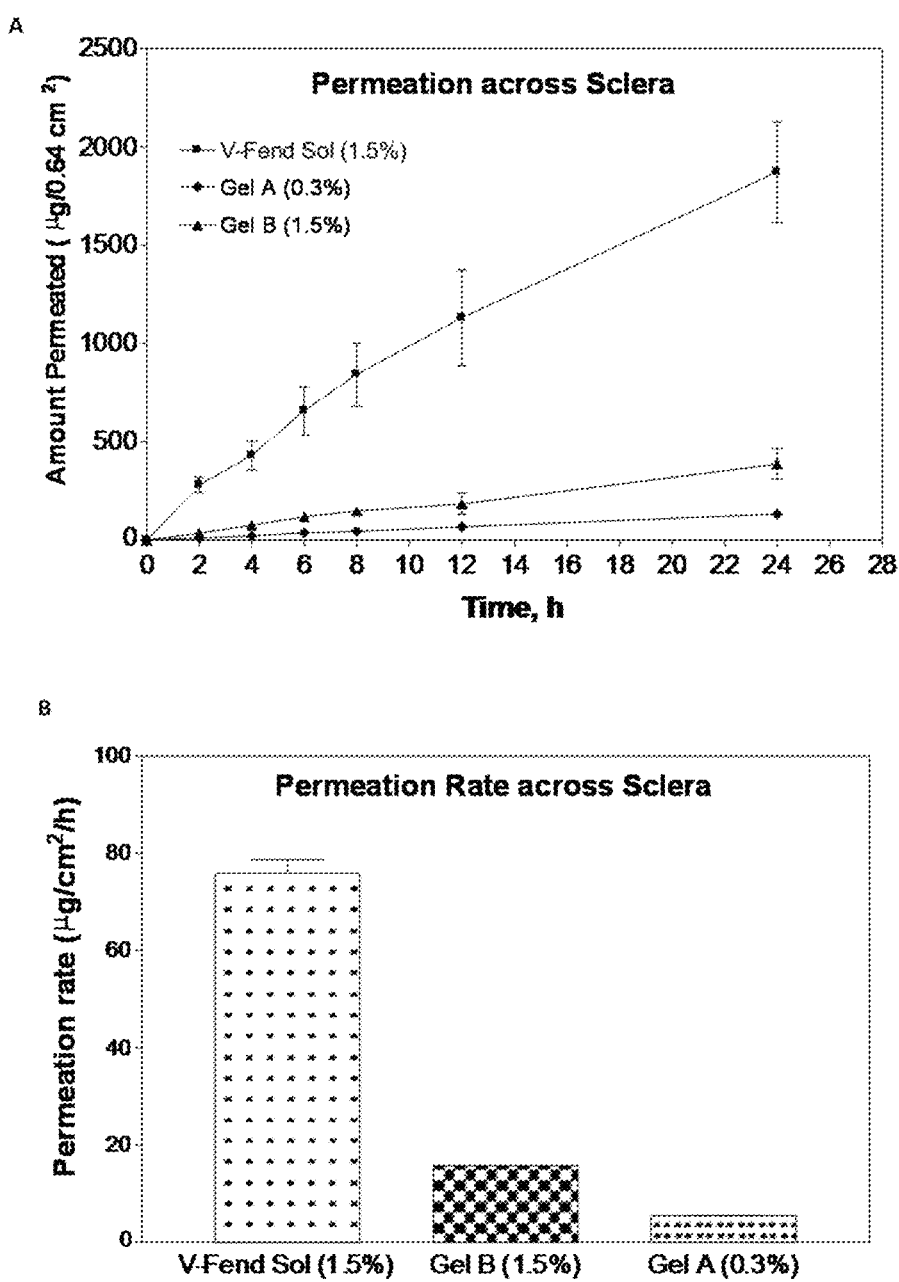
FIGS. 17A-17B show the permeation of voriconazole across the sclera over time (FIG. 17A) and the permeation rate across the sclera (FIG. 17B). A concentration dependent increase in the permeation of voriconazole from the thermogel formulations was noted. Gel B (1.5% voriconazole-thermogel) showed significantly lower permeation as compared to the 1.5% voriconazole solution.
Figures 18A, 18B, 18C, 18D:
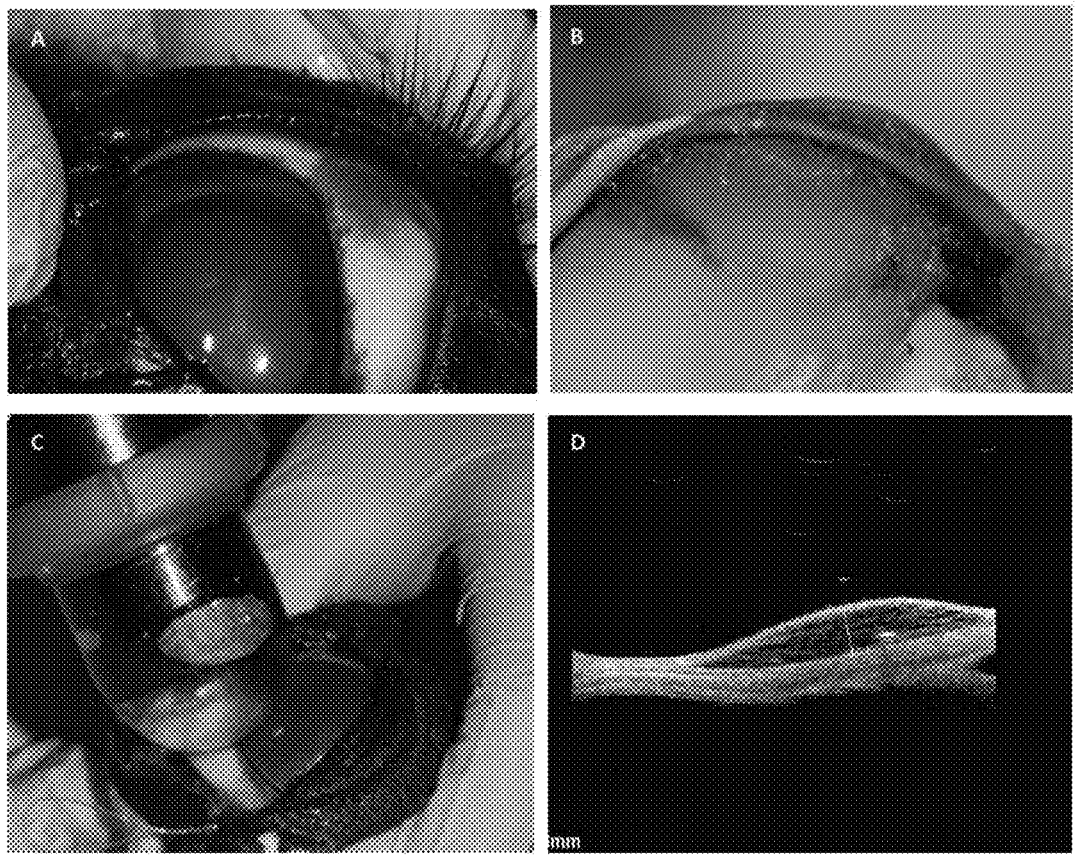
FIGS. 18A-18D show 300 μl PLGA-PEG-PLGA thermogel deposit in the dorsal bulbar SCS of an ex vivo equine eye.

Voriconazole displayed sustained release from the thermogel throughout the study period for all formulations, with peak release occurring on day 1 (see FIGS. 12 and 13). Voriconazole release from the thermogel followed first-order kinetics with release t1/2 ranging from 1.82 (Group 3) to 4.22 days (Group 2) (see Table 1 and FIG. 14).

TABLE 1

Release kinetics of voriconazole from the thermogel in vitro

| | Group 2 Mean | SD | Group 3 Mean | SD | | Group 4 Mean | SD | Group 5 Mean | SD | | Group 6 Mean | SD |
|---|---|---|---|---|---|---|---|---|---|---|---|---|
| UC24 (µg*day/ml) | 1276 | 309 | 696 | 88 | * | 3583 | 1066 | 2871 | 258 | | 4133 | 2498 |
| UC28 (µg*day/ml) | 1293 | 312 | 696 | 88 | * | 3637 | 1098 | 2877 | 257 | | 4135 | 2498 |
| K release (1/day) | 0.1642 | 0.0021 | 0.3968 | 0.0931 | * | 0.1915 | 0.0283 | 0.2613 | 0.0101 | * | 0.7558 | 0.3043 |
| r | 0.9646 | 0.0207 | 0.9962 | 0.0029 | | 0.9949 | 0.0030 | 0.9939 | 0.0041 | | 0.9847 | 0.0032 |
| t½ release (day) | 4.220 | 0.056 | 1.823 | 0.487 | * | 3.678 | 0.592 | 2.654 | 0.100 | * | 1.050 | 0.506 |

The concentrations released exceeded the target MIC (0.5 µg/ml) for 28 days in Groups 2 and 4 and 16 days in Groups 3 and 5 (FIG. 12). There was no voriconazole detected at any time in samples from the negative control group (Group 1), and voriconazole was undetectable by day 6 in the positive control group (Group 6). The addition of ethanol altered the nature of voriconazole release from the thermogel.

Phase separation of the thermogel into liquid and gel components occurred within the first 24 hours in all groups. Visual degradation of the thermogel occurred in all test groups from day 9 of the study. Greater thermogel breakdown occurred in the groups without ethanol (groups 1, 2 and 4), in which approximately 30% of the original volume remained at day 28 compared to those with ethanol (groups 3 and 5), in which approximately 50% remained at day 28 (see FIGS. 15A-15D).

EXAMPLE 6

Corneal and Scleral Penetration of Voriconazole Released from a PLGA-PEG-PLGA Thermogel In Vitro This example investigates diffusion of voriconazole from an exemplary PLGA-PEG-PLGA thermogel and across isolated equine corneas and sclerae using an in vitro Franz Cell diffusion model. The rates of diffusion of voriconazole (topical 1.5% vs. thermogel) were compared across isolated equine corneas and sclerae in an in vitro Franz Cell diffusion model.

In Vitro Corneal and Scleral Voriconazole Permeation

Five eyes were obtained from horses free from corneal and scleral disease that were euthanized at the AULATH for reasons not related to this example. Enucleation was performed immediately following euthanasia. Enucleated eyes were placed in 0.9% saline (Baxter Healthcare Corporation, Deerfield, Ill.) and transported on ice to the laboratory within 20 minutes of enucleation, where 2 paracentral corneal and 2 dorsal scleral buttons were harvested from each eye via the use of a 16 mm corneal trephine (Asico, LLC, Westmont, Ill.) and Castroviejo corneal and Westcott tenotomy scissors.

In vitro permeation studies were performed on vertical static Franz diffusion cells (PermeGear, Hellertown, Pa., USA). The harvested corneal and scleral buttons were rinsed free of proteinaceous material with 0.9% saline and placed horizontally between the donor and receptor halves of individual cells (diffusion area 0.64 cm$^2$), with the epithelial surface of the corneal buttons and the external surface of the scleral buttons facing the donor compartment. The receiver chamber contained PBS (5 ml, pH 7.4), that was maintained at 34° C. with a water circulation jacket surrounding the lower part of the cell. Stirring in the receptor was maintained with the help of a magnetic bead. Three tests groups were determined and the donor compartment loaded with either 300 µl of a 1.5% voriconazole solution previously shown to penetrate equine corneas in vivo (Vfend, Pfizer, New York, N.Y.; control group), 300 µl thermogel combined with 1 mg voriconazole (Gel A; 0.3% voriconazole-thermogel) or 300 µl thermogel combined with 5 mg voriconazole (Gel B; 1.5% voriconazole-thermogel). PBS samples were taken from the receptor chamber and the receptor chamber was replenished with a fresh 1 ml PBS at 0, 2, 4, 6, 8, 12, and 24 hours. Samples were stored at −80° C. until the completion of sampling and then analyzed for voriconazole content via reverse phase HPLC. Each group was tested in triplicate.

After 24 hours, each corneal button was rinsed 3 times with PBS to remove any remaining voriconazole or thermogel, blotted dry and the 'wet weight' (Wa) recorded. The corneal samples were then desiccated at 70° C. in an incubator for 8 hours and the 'dry weight' (Wb) recorded. From these data the percentage of corneal hydration was calculated (% corneal hydration=[1−(Wa/Wb)]×100), with a limit of 83% corneal hydration for individual corneal buttons set for inclusion of results in the study.

High-Performance Liquid Chromatography

The drug release and permeation test PBS samples were analyzed by reverse phase HPLC. Briefly, the HPLC system (Agilent 1200 series) consisted of pumps, an auto sampler, UV/visible light absorption detector, column (Thermo Beta-Basic-18, 4.6 mm·15 cm, 5µ; Bellefonte, Pa., USA), and computer interface. The mobile phase consisted of 35% 0.1 M N, N, N, N-tetramethylenediamine (Fisher Scientific, Inc., Waltham, Mass., USA) and methanol (Fisher Scientific, Inc.), at a flow rate of 1.0 ml/min at room temperature. The injection volume was 100 µl. Voriconazole and ketoconazole, the internal standards, were detected at a wavelength of 254 nm, and the retention times were 3.7 and 13.5 minutes respectively. Calibration standards with voriconazole concentrations in dissolution and selected fluids ranging from 1.0 to 100 µg/ml were prepared. The lower limit of detection for voriconazole was 1 µg/ml, and the lower limit of quantification was 0.5 µg/ml. Intra- and inter-day variations were 4.0% and 5.1% respectively.

Permeation of voriconazole through the cornea and sclera was observed for all formulations (see FIG. 16A-16B and FIG. 17A-17B). The sclera was two-fold more permeable than the cornea to the 1.5% voriconazole solution (P<0.001). Both conical- and scleral-permeation data demonstrated a concentration dependent increase in the permeation of voriconazole from the thermogel formulations. The permeation rate through the sclera or cornea for Gel B (1.5% voriconazole-thermogel) was at least 3-fold higher than that of Gel A (0.3% voriconazole-thermogel) (P<0.001). Gel B (1.5% voriconazole-thermogel) showed significantly lower permeation as compared to the 1.5% voriconazole solution through both the sclera and cornea. Corneal hydration was less than 83% in all cases (range: 78.3-82.9%; mean±standard deviation: 81.5%±1.9%) (See Table 2).

TABLE 2

Corneal hydration values following the Franz cell diffusion study.
C1-3: 1.5% voriconazole solution, C4-6: Gel A (0.3% voriconazole thermogel), C7-9: Gel B (1.5% voriconazole thermogel).

| Sample number | Wet weight | Dry weight | Percent (%) reduction |
|---|---|---|---|
| C1 | 95.4 | 20.7 | 78.3 |
| C2 | 82.5 | 17.8 | 78.4 |
| C3 | 114 | 19.5 | 82.9 |
| C4 | 113.2 | 21.4 | 81 |
| C5 | 142.3 | 24.5 | 82.7 |
| C6 | 101.7 | 18.1 | 82.2 |
| C7 | 115.8 | 20.2 | 82.6 |
| C8 | 100.5 | 17.2 | 82.9 |
| C9 | 106.4 | 18.3 | 82.8 |

Transconjunctival permeation followed by corneal absorption, reflux out of the injection site, and direct penetration through the sclera are all proposed mechanisms of transport of medication to the anterior chamber following subconjunctival injection. Scleral permeation was two-fold higher than corneal permeation for the 1.5% voriconazole solution in this study, indicating successful delivery of voriconazole through the sclera following subconjunctival injection. This discrepancy is likely the result of structural and physiological differences between the tissues tested. The sclera has 10 times fewer glycosaminoglycans than the cornea, and the scleral stroma has a greater degree of fibrillar interweave than the corneal stroma.

Similar permeation rates were identified across both tissues in the 1.5% and 0.3% voriconazole-thermogel formulations, further supporting the validity of these thermogels as vehicles for sustained ophthalmic drug delivery, as permeation is concentration dependent and this finding likely reflects lower exposure of the sclera to voriconazole in the thermogel groups as it was slowly being released from the thermogels than in the solution group.

Despite the lower permeation of the voriconazole through tissues following release from the thermogel than when applied as a solution alone, the thermogels still show significant potential for use in the treatment of fungal ocular infections as the controlled and sustained achievement of therapeutic concentrations of the medication in the cornea and anterior chamber is the goal of therapy and this can be achieved in this case by a single injection of thermogel as opposed to multiple topical applications of voriconazole solution.

EXAMPLE 7

Characteristics of Voriconazole-PLGA-PEG-PLGA Thermogel Injected Subconjunctivally in Ex Vivo Equine Eyes This example investigates the technique for injecting voriconazole-PLGA-PEG-PLGA thermogel subconjunctivally in the horse in an ex vivo and in vivo model. Formation of a discrete gel deposit in the SCS is also demonstrated following injection of liquid (4° C.) voriconazole-PLGA-PEG-PLGA thermogel into equine eyes via ultrasound biomicroscopy (UBM) examination and tissue dissection.

Ten eyes were obtained from horses free from corneal and scleral disease that were euthanized at the AULATH, for reasons not related to this study. Enucleation was performed immediately following euthanasia via a transpalpebral approach, and the thermogel was injected immediately following enucleation. The temperature in the ventral bulbar SCS was measured immediately prior to injection to ensure normothermia was maintained following enucleation. The thermogel (300 µl) in its liquid state (4° C.) was injected under the dorsal bulbar conjunctiva through a 30-gauge needle and the ease of injection and time taken to gel formation recorded. High-frequency (50 MHz) UBM (Aviso™, 2016 Quantel Medical, Bozeman, US) was performed in order to visualize the thermogel deposit, describe its location and shape, and measure its dimensions. The eyes were then frozen with liquid nitrogen, sectioned using a microtome blade and the gross appearance of the gel deposit was further described.

The thermogel was able to be easily injected into the dorsal bulbar SCS through a 30-gauge needle in all cases. A discrete gel deposit was formed in the SCS which was able to be observed both grossly and as a well-demarcated hypoechoic structure via UBM (see FIGS. 18A-18D). The deposits formed were small and ovoid with length 15.1±1.37 mm, width 10.1 mm±1.65 mm and maximum depth 1.3±0.25 mm (0.83-1.72 mm). Gelation occurred rapidly, with a mean time from initiation of the injection to gelation of 16.4±1.65 seconds (14-19 seconds) (see Table 3).

TABLE 3

Measurements of dorsal bulbar SCS thermogel deposits obtained after injecting ten ex vivo equine eyes with 300 µl PLGA-PEG-PLGA thermogel.

| Eye number | Caliper measurements (mm) | | U/S measurement (mm) Max. Depth | Bulbar SCS Temperature | Time to gel (seconds) |
|---|---|---|---|---|---|
| | Length | Width | | | |
| 1 | 15 | 9 | 1.48 | 31 | 15 |
| 2 | 14 | 10 | 1.44 | 33 | 18 |
| 3 | 13 | 8 | 1.72 | 31.6 | 19 |
| 4 | 16 | 10 | 1.13 | 33 | 16 |
| 5 | 16 | 14 | 0.83 | 31.4 | 14 |
| 6 | 17 | 11 | 1.45 | 35.2 | 15 |
| 7 | 14 | 10 | 1.46 | 34.5 | 17 |
| 8 | 17 | 11 | 1.16 | 33.4 | 18 |
| 9 | 14 | 10 | 1.33 | 33.2 | 17 |
| 10 | 15 | 12 | 1.47 | 33.2 | 15 |

EXAMPLE 8

Short- and Midterm Ocular Toxicity Pilot Study in a Live Horse

This example investigates the technique for injecting an exemplary voriconazole-PLGA-PEG-PLGA thermogel subconjunctivally in the horse in an in vivo model. Safety of the injection is demonstrated through clinical and histopathologic examination of treated eyes 2 hours and 7 days post injection of the composition.

Short- and Mid-Term Toxicity Pilot Study in a Single Live Horse

Following validation of procedures ex vivo, the purpose of this portion was to evaluate short-term (2 hours) and mid-term (7 days) clinical tolerance of, and histopathologic changes following, SCS injection of voriconazole-containing thermogel in a pilot study in a healthy adult horse.

The horse was sedated with 5 mg detomidine hydrochloride (Dormosedan; Zoetis Inc., Florham Park, N.J.) and 5 mg butorphanol tartrate (Torbugesic; Zoetis Inc., Florham Park, N.J.) intravenously and local ocular anesthesia was supplied through administration of perineural 2% lidocaine hydrochloride (Hospira Inc., Lake Forest, Ill.) around the auriculopalpebral and frontal nerves and topical 0.5% proparacaine hydrochloride (Akorn Inc., Lake Forest, Ill.). The eye was prepped with sterile diluted 5% betadine solution, irrigated with sterile eyewash (Purdue Products L.P., Stamford, Conn.) and 300 µl 1.5% voriconazole thermogel was injected into the right dorsal bulbar SCS through a 30-gauge needle. Flunixin meglumine (1.1 mg/kg IV; Banamine®, Intervet International, Germany) was administered immediately post injection and topical ocular neomycin-polymixin-bacitracin ointment (Vetropolycin®, Dechra Veterinary Products, Overland Park, Kans.) was applied to the treated eye every 6 hours for the 48 hours following injection. A complete ophthalmic examination including Schirmer tear test (STT, Schering-Plough, Charlotte, N.C.), biomicroscopy examination (Kowa SL-14, Tokyo, Japan), Tonovet tonometry (iCare, Finland), fluorescein test (Akorn Inc., Buffalo Grove, Ill.), and funduscopy was performed 1 day before and 7 days after the SCS injection. After pupillary dilation with tropicamide 1% (Akorn Inc., Buffalo Grove, Ill.), the ocular fundus was photographed (Optibrand Clearview, Optibrand Ltd., Fort Collins Colo.). The horse was examined twice daily and monitored closely for signs of inflammation, reaction or pain in the treated eye. A modified Hackett-McDonald microscopic ocular inflammatory scoring system was used to evaluate the ocular anterior segment and anterior vitreous. Scores of the conjunctiva (congestion; swelling; discharge; 0-4); aqueous flare (0-3); pupillary light reflex (0-2); iris involvement (0-4); cornea (involvement and area; 0-4); pannus (vascularization; 0-2); and anterior vitreal cellular infiltrate (0-4) were summed to provide a single inflammatory score for each examination. Seven days post-injection the horse was placed under general anesthesia then euthanized for reasons not related to this example. Following anesthetic induction (2 hours prior to euthanasia) 300 µl of a 1.5% voriconazole thermogel was injected into the left dorsal bulbar SCS. Following euthanasia, both of the horse's eyes were enucleated and submitted for histopathologic examination.

Data Analysis

Descriptive statistics (mean, median, range) were calculated for measurements of thermogel deposit dimensions obtained following ex vivo SCS injection and percentage corneal hydration following in vitro permeation studies (Microsoft Excel 2013, Microsoft, Richmond, Wash.). All data were expressed as mean±standard deviation. For the release study, rates of release and transfer were obtained from slopes of cumulative amounts released, unreleased, and transferred based on linear and log co-ordinates. For first-order release, half-life (t1/2) was estimated as 0.693 divided by the first-order rate constant. For the permeation study, the cumulative amount of voriconazole released from the thermogel as well the amounts permeated across cornea and sclera were plotted as a function of time. The slope of the linear portion of the permeation plot was presented as permeation rate ($\mu g/cm^2/h$). Data were analyzed by one-way ANOVA followed by Dunnett's test to determine the level of significance between various groups. The data were considered significant at $P<0.05$. Data were analyzed using a commercial statistical analysis program (GraphPad Prism software version 5, La Jolla, Calif.).

Figure 19:
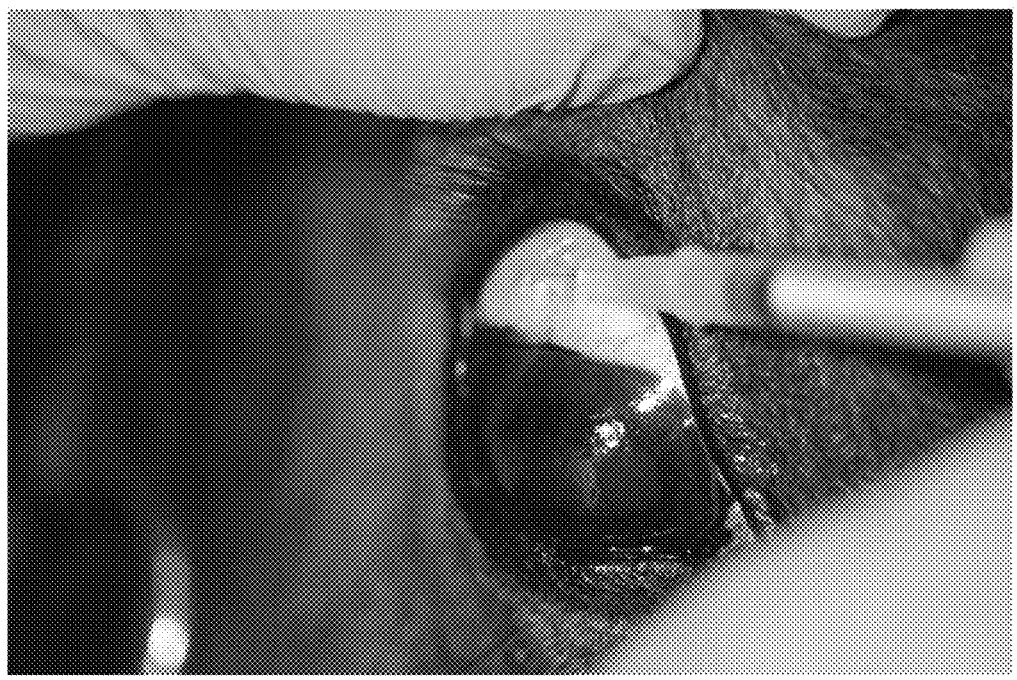
FIG. 19 shows in vivo injection of 300 μl thermogel in the right eye of a horse following administration of sedation and local anesthetic agents.
Figures 20A, 20B, 20C, 20D:
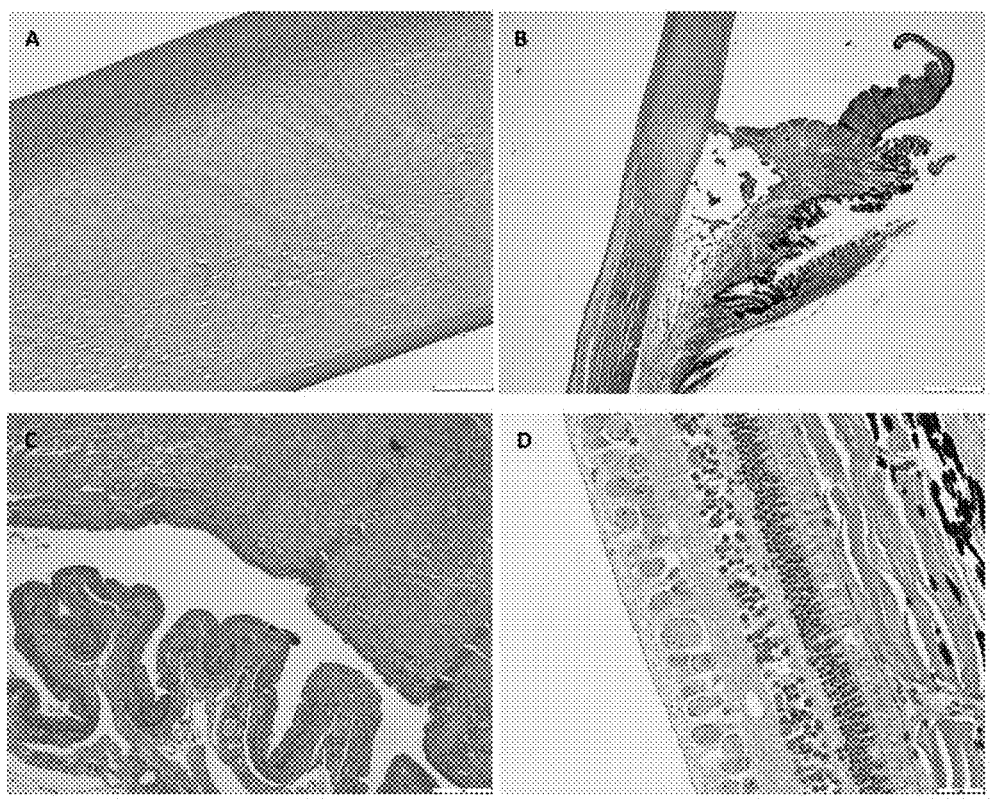
FIGS. 20A-20D show histopathologic sections (hematoxylin and eosin) from the right eye of a horse injected with 300 μl thermogel in the right dorsal bulbar SCS seven days prior to enucleation.

Dorsal bulbar SCS injection of the voriconazole-containing thermogel was easily performed and well tolerated in vivo following administration of intravenous sedation and local anesthesia (see FIG. 19). The thermogel remained in liquid form when stored in syringes in a cooler during the time it took to administer local anesthesia and perform a sterile preparation of the eye, and converted to a gel state within 10 seconds of completing the injection. No local or systemic adverse reactions were noted in the treated eye in the 7 days following injection, with the exception of self-limiting chemosis and conjunctival hyperemia on days 2 and 3 post-injection. Twice daily ocular examination from a distance, physical examination and complete ophthalmic examination 7 days post-injection, all returned normal findings, and the treated horse exhibited normal attitude, feed and water intake and fecal and urine output throughout the entire study period. The conjunctiva, sclera, cornea, lens, retina and optic nerve of both eyes were normal on histologic examination, with no evidence of inflammation or tissue damage observed either 7 days or 2 hours post-thermogel injection (see FIG. 20A-20D).

In conclusion, the veterinary formulations of the present disclosure were relatively easy to inject into the dorsal bulbar SCS of normothermic ex vivo equine eyes through a 30 gauge needle, in a manner typical of current practices of SCS injections in the clinical setting, and formed a discrete gel deposit within 20 seconds of injection. This deposit was identifiable both grossly and via UBM. The method was repeatable in a live pilot horse understanding sedation and local anesthesia and was able to be performed by an equine veterinarian without ophthalmology specialty training, following demonstration of the technique by a veterinary ophthalmologist.

Furthermore, the presence of the small gel deposit in the dorsal bulbar SCS was well tolerated by the horse, and no evidence of toxicity was identified on clinical or histopathologic ocular examination either 2 hours or 7 days post-thermogel injection. These findings suggest that SCS injection of the veterinary formulations could be performed practically and safely by veterinarians in animals experiencing keratomycosis.

What is claimed is:

1. A method of treating a fungal infection in an equine, said method comprising the step of administering a veterinary formulation comprising i) a therapeutically effective amount of voriconazole, ii) a thermogel polymer, and iii) ethanol to the equine via an injection in a subconjunctival space (SCS) of the equine,
    wherein the thermogel polymer consists of a combination of a first PLGA-PEG-PLGA composition with a molecular weight of 1100:1000:1100 Da and a second PLGA-PEG-PLGA composition with a molecular weight of 1500:1500:1500 Da,
    wherein the first PLGA-PEG-PLGA composition and the second PLGA-PEG-PLGA composition are present at a ratio of about 1:1,
    wherein upon the injection to the equine, the thermogel polymer of the veterinary formulation is a liquid and wherein the liquid thermogel polymer forms a gel deposit in the SCS of the equine subsequent to the injection.

2. The method of claim 1, wherein the fungal infection causes keratomycosis in the equine.

3. The method of claim 1, wherein the voriconazole diffuses through a cornea of the equine.

4. The method of claim 1, wherein the voriconazole diffuses through a sclera of the equine.

5. The method of claim 1, wherein the administration provides a concentration of voriconazole greater than the target minimum inhibitory concentration for about 7 days.

6. The method of claim 1, wherein the administration provides a concentration of voriconazole greater than the target minimum inhibitory concentration for about 14 days.

7. The method of claim 1, wherein the gel deposit is formed at a temperature of about 30° C. to about 40° C.

8. The method of claim 1, wherein the therapeutically effective amount of the voriconazole is at a dose of about 0.001 to about 1 mg/kg of weight of the equine.

9. The method of claim 1, wherein the voriconazole is released from the thermogel polymer at a rate between about 100 μg/day to about 10,000 μg/day.

* * * * *